US012613336B2

(12) United States Patent
Xie et al.

(10) Patent No.: US 12,613,336 B2
(45) Date of Patent: Apr. 28, 2026

(54) ULTRASOUND IMAGING WITH ANATOMY-BASED ACOUSTIC SETTINGS

(71) Applicant: KONINKLIJKE PHILIPS N.V., Eindhoven (NL)

(72) Inventors: Hua Xie, Cambridge, MA (US); Claudia Errico, Medford, MA (US); Shyam Bharat, Arlington, MA (US); Kyong Chang, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 18/268,153

(22) PCT Filed: Dec. 10, 2021

(86) PCT No.: PCT/EP2021/085123
§ 371 (c)(1),
(2) Date: Jun. 16, 2023

(87) PCT Pub. No.: WO2022/128759
PCT Pub. Date: Jun. 23, 2022

(65) Prior Publication Data
US 2024/0053470 A1 Feb. 15, 2024

Related U.S. Application Data

(60) Provisional application No. 63/127,475, filed on Dec. 18, 2020.

(51) Int. Cl.
*G01S 15/89* (2006.01)
*A61B 8/00* (2006.01)
(Continued)

(52) U.S. Cl.
CPC ........ *G01S 15/8952* (2013.01); *A61B 8/0858* (2013.01); *A61B 8/14* (2013.01);
(Continued)

(58) Field of Classification Search
CPC ..... A61B 8/469; A61B 8/4245; A61B 8/4254; A61B 8/4488; G01S 15/8952
See application file for complete search history.

(56) References Cited

U.S. PATENT DOCUMENTS

2005/0096543 A1* 5/2005 Jackson ................. G06T 7/248
600/441
2005/0240103 A1 10/2005 Byrd et al.
(Continued)

FOREIGN PATENT DOCUMENTS

CN 110974298 A 4/2020
EP 1781176 B1 * 4/2011 ............. A61B 5/204
(Continued)

OTHER PUBLICATIONS

International Search Report and Written Opinion for PCT/EP2021/085123; Mailing date: Jul. 22, 2022, 22 pages.
(Continued)

*Primary Examiner* — Nyrobi Celestine

(57) ABSTRACT

An ultrasound imaging system includes an array of acoustic elements and a processor circuit configured for communication with the array of acoustic elements. The processor circuit may be configured to control the array of acoustic elements to transmit first ultrasound energy at a first frequency and receive echoes associated with the first ultrasound energy. The processor circuit may be configured to identify an acoustic window based on the echoes associated with the first ultrasound energy and determine a second frequency based on the acoustic window. The processor circuit may be configured to control the array of acoustic elements to transmit second ultrasound energy at the second frequency and receive echoes associated with the second ultrasound energy. The processor circuit may be configured to generate an image based on the echoes associated with the
(Continued)

second ultrasound energy and to output the image to a display in communication with the processor circuit.

15 Claims, 12 Drawing Sheets

(51) Int. Cl.

| | |
|---|---|
| *A61B 8/08* | (2006.01) |
| *A61B 8/14* | (2006.01) |
| *G01S 7/52* | (2006.01) |

(52) U.S. Cl.
CPC .......... *A61B 8/4254* (2013.01); *A61B 8/4488* (2013.01); *A61B 8/463* (2013.01); *A61B 8/469* (2013.01); *A61B 8/54* (2013.01); *G01S 7/52057* (2013.01); *G01S 15/8915* (2013.01)

(56) References Cited

U.S. PATENT DOCUMENTS

| | | | |
|---|---|---|---|
| 2013/0253325 A1* | 9/2013 | Call | A61B 8/54 |
| | | | 600/447 |
| 2016/0143617 A1 | 5/2016 | Ebbini et al. | |
| 2016/0199029 A1 | 7/2016 | Struiuk et al. | |
| 2017/0071579 A1* | 3/2017 | Ko | A61B 8/546 |
| 2018/0055479 A1 | 3/2018 | Lalena | |
| 2018/0125448 A1 | 5/2018 | Karadayi | |
| 2018/0256075 A1* | 9/2018 | Souzy | A61B 5/6823 |
| 2019/0328361 A1* | 10/2019 | Halmann | G06T 3/4038 |
| 2020/0046314 A1* | 2/2020 | Neben | A61B 8/54 |
| 2020/0054306 A1* | 2/2020 | Mehanian | A61B 8/5223 |
| 2020/0352547 A1* | 11/2020 | Raju | A61B 8/5269 |
| 2021/0045711 A1* | 2/2021 | Brattain | A61B 8/0875 |
| 2021/0128114 A1* | 5/2021 | Patil | A61B 8/54 |
| 2021/0145399 A1* | 5/2021 | Xie | A61B 8/461 |
| 2021/0219961 A1* | 7/2021 | Toyonaga | G01S 15/895 |
| 2021/0350539 A1* | 11/2021 | Halmann | A61B 8/5246 |
| 2022/0160334 A1* | 5/2022 | Venkataramani | A61B 8/085 |
| 2022/0198669 A1* | 6/2022 | Chen | G06T 7/0016 |

FOREIGN PATENT DOCUMENTS

| | | | |
|---|---|---|---|
| WO | 2006031526 A1 | 3/2006 | |
| WO | 2017076758 A1 | 5/2017 | |
| WO | 2018158283 A1 | 9/2018 | |
| WO | 2022128838 A1 | 6/2022 | |

OTHER PUBLICATIONS

Roriz, D. et al., "Ultrasound in the evaluation of diaphragm", European Society of Radiology, ECR, 2015, 16 pages.
Sarwal, A. et al., "Neuromuscular ultrasound for evaluation of the diaphragm", Muscle & Nerve, 2013, vol. 47, Issue 3, pp. 319-329.
Haaksma, M. et al., "Ultrasound imaging of the diaphragm: Facts and future. A guide for the bedside clinician", Neth J Crit Care 2018, vol. 26, No. 2, pp. 58-63.
Qian, Z. et al., "Ultrasound assessment of diaphragmatic dysfunction as a predictor of weaning outcome from mechanical ventilation: a systematic review and meta-analysis", BMJ Open 2018, vol. 8:e021189, 10 pages.
Zambon, M. et al., "Assessment of diaphragmatic dysfunction in the critically ill patient with ultrasound: a systematic review", Intensive Care Med, 2017, vol. 43, pp. 29-38.
Li, C. et al., "Diaphragmatic ultrasonography for predicting ventilator weaning: a meta-analysis", Medicine, 2018, vol. 97, No. 22:e10968, 10 pages.
Kelley, R. et al., "Diaphragm abnormalities in heart failure and aging: mechanisms and integration of cardiovascular and respiratory pathophysiology", Heart Fail Rev., 2017, vol. 22, Issue 2, pp. 191-207.
Dubé, B-P. et al., "Diaphragm Dysfunction: Diagnostic Approaches and Management Strategies", J Clin Med., 2016, vol. 5, Issue 12, 20 Pages.
McCool, F. et al., "Dysfunction of the diaphragm", N Engl J Med, 2012, Abstract Only.
Cardenas, L.Z. et al., "Diaphragmatic Ultrasound Correlates with Inspiratory Muscle Strength and Pulmonary Function in Healthy Subjects", Ultrasound in Medicine & Biology, 2018, vol. 44, Issue 4, pp. 786-793.
Llamas-Álvarez, A. et al., "Diaphragm and Lung Ultrasound to Predict Weaning Outcome: Systematic Review and Meta-Analysis", Chest, 2017, vol. 152, No. 6, pp. 1140-1150.
Lee, E-P et al., "Evaluation of diaphragmatic function in mechanically ventilated children: An ultrasound study", PLoS One. 2017; vol. 12, No. 8, 11 pages.
Samanta, S. et al., "Diaphragm thickening fraction to predict weaning—a prospective exploratory study", J Intensive Care, 2017, vol. 5:62, 9 pages.
Farghaly, S. et al., " Diaphragm ultrasound as a new method to predict extubation outcome in mechanically ventilated patients", Australian Critical Care, 2017, vol. 30, Issue 1, pp. 37-43.
Bachasson, D. et al., "Ultrafast Ultrasound Imaging Grants Alternate Methods for Assessing Diaphragm Function", IEEE International Ultrasonics Symposium , 2018, 4 pages.
Anonymous, "Symptoms of Disorders of the Diaphragm", retrieved from https://www.nm.org/conditions-and-care-areas/pulmonary/diaphragmatic-hernia/symptoms, 2023, 2 pages.

* cited by examiner

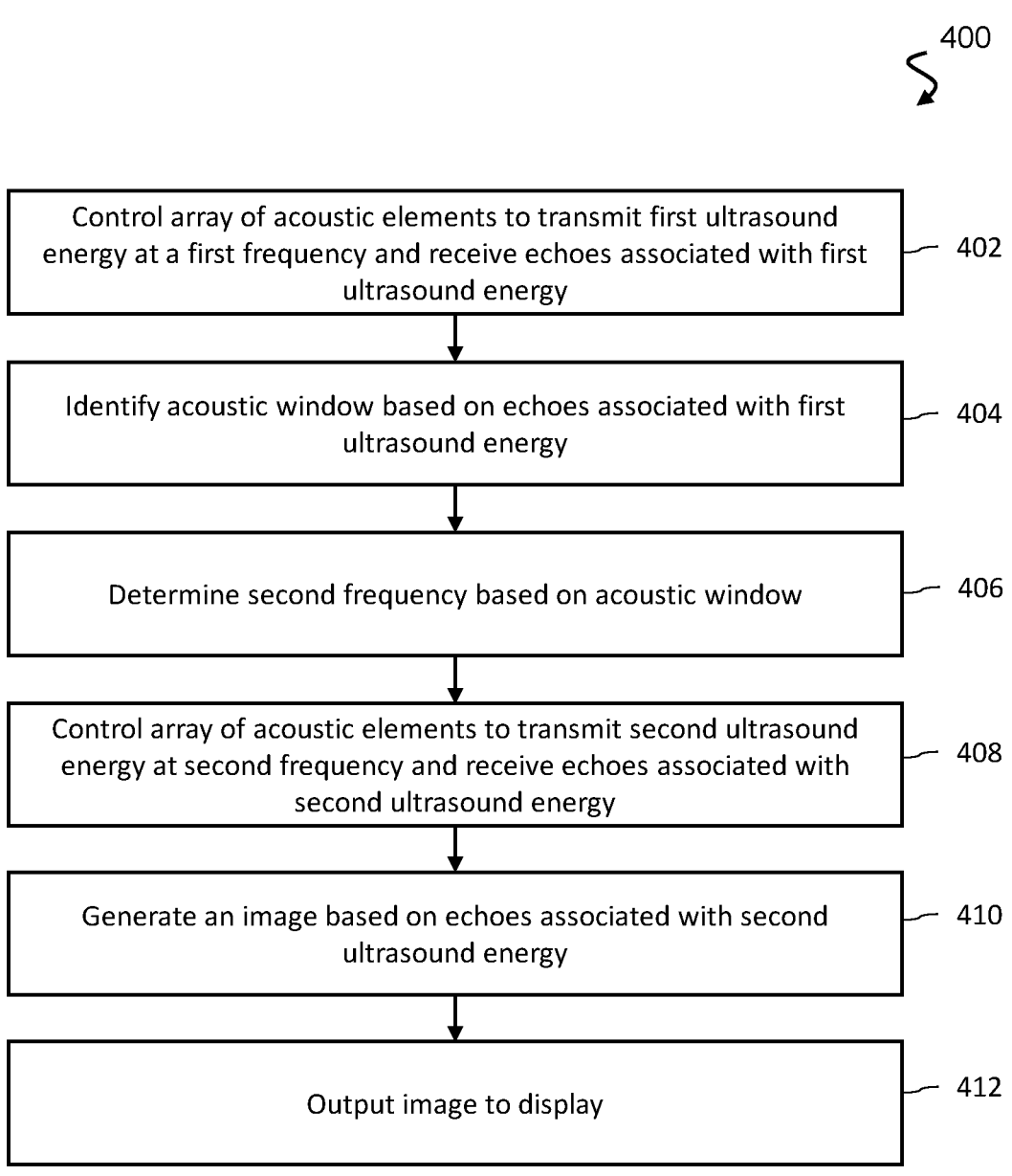

400

Control array of acoustic elements to transmit first ultrasound energy at a first frequency and receive echoes associated with first ultrasound energy — 402

Identify acoustic window based on echoes associated with first ultrasound energy — 404

Determine second frequency based on acoustic window — 406

Control array of acoustic elements to transmit second ultrasound energy at second frequency and receive echoes associated with second ultrasound energy — 408

Generate an image based on echoes associated with second ultrasound energy — 410

Output image to display — 412

FRC Thickness (TFRC) = 0.20cm

1120

1122      1124

TLC Thickness (TTLC) = 0.40cm

ULTRASOUND IMAGING WITH ANATOMY-BASED ACOUSTIC SETTINGS

CROSS-REFERENCE TO PRIOR APPLICATIONS

This application is the U.S. National Phase application under 35 U.S.C. § 371 of International Application No. PCT/EP2021/085123, filed on Dec. 10, 2021, which claims the benefit of Provisional Patent Application No. 63/127,475, filed on Dec. 18, 2020. These applications are hereby incorporated by reference herein.

TECHNICAL FIELD

The present disclosure relates generally to ultrasound imaging. For example, an ultrasound imaging system can adaptively tune an acoustic setting, such as a frequency, used in the transmission and/or reception of ultrasound energy based on an identified acoustic window and/or anatomical feature.

BACKGROUND

The diaphragm is a thin, dome-shaped muscle that is used to facilitate respiration. During a respiratory (e.g., breathing) cycle, for example, the diaphragm contracts and moves downward for inhalation and relaxes for exhalation. Assessments of diaphragm characteristics (e.g., function) during the respiratory cycle may provide predictors for diaphragm contractile dysfunction, such as diaphragm atrophy or paralysis. In particular, measurements of diaphragm excursion (e.g., the global displacement of the diaphragm over the respiratory cycle), as well as measurements related to the thickness of the diaphragm over the respiratory cycle may be used for diagnostic purposes.

Ultrasound imaging may be used to assess the above-mentioned diaphragm characteristics. More specifically, ultrasound imaging of different parts of the diaphragm (e.g., the zone of apposition and/or the zone of dome) may be used to obtain measurements of diaphragm thickness and excursion. The imaging procedure used to obtain ultrasound images of the zone of apposition may vary from the imaging procedure used to obtain ultrasound images of the zone of dome. For instance, because of the relative locations of the zone of dome and zone of apposition, a sonographer may place an ultrasound probe at a different position on a patient to image each zone. Further, ultrasound energy with different frequencies may be used to image the zone of apposition and the zone of dome because they are located at different depths. These procedural differences, coupled with the movement of the diaphragm during respiration and the variance of the diaphragm from patient to patient, complicate the reliable imaging and assessment of the diaphragm via manual techniques.

SUMMARY

Embodiments of the present disclosure are systems, devices, and methods for automatically identifying an acoustic window associated with an ultrasound image using a deep learning network and adjusting acoustic settings, such as a frequency, associated with ultrasound transmission and/or reception based on the identified acoustic window. For instance, based on the identification of an acoustic window associated with imaging the zone of dome of a diaphragm, the frequency may be tuned to a relatively low frequency, and based on the identification of an acoustic window associated with imaging the zone of apposition of the diaphragm, the frequency may be tuned to a relatively high frequency. Moreover, in some cases, additional or alternative acoustic settings maybe tuned. For instance, the beam steering angle associated with the ultrasound transmission and/or reception may be adaptively selected to an angle that results in the highest echogenicity and/or an echogenicity satisfying a threshold for the diaphragm. As such, the zone of dome and zone of apposition of a diaphragm may be reliably imaged and characterized with an improved image quality. In this way, errors resulting from manual identification of anatomical features and manual control of acoustic settings may be reduced. In addition, quantitative measurements of diaphragm characteristics may be automatically performed based on ultrasound imaging data collected in accordance with the optimized acoustic settings. To that end, measurement accuracy and reproducibility may be improved with respect to manual measurement procedures.

In an exemplary aspect, an ultrasound imaging system includes an array of acoustic elements and a processor circuit configured for communication with the array of acoustic elements. The processor circuit may be configured to: control the array of acoustic elements to transmit first ultrasound energy at a first frequency and receive echoes associated with the first ultrasound energy; identify an acoustic window based on the echoes associated with the first ultrasound energy; determine a second frequency based on the acoustic window; control the array of acoustic elements to transmit second ultrasound energy at the second frequency and receive echoes associated with the second ultrasound energy; generate an image based on the echoes associated with the second ultrasound energy; and output the image to a display in communication with the processor circuit.

In some aspects, the processor circuit may be configured to identify the acoustic window further based on an orientation of the array of acoustic elements. In some aspects, the processor circuit may be configured to identify the acoustic window further based on a user input. In some aspects, the user input includes at least one of depth setting or a selection of an anatomical feature. In some aspects, the ultrasound imaging system further includes an inertial measurement unit (IMU) in communication with the processor circuit. In such aspects, the processor circuit may be configured to identify the acoustic window further based on data collected at the IMU.

In some aspects, the processor circuit may be further configured to: generate image data based on the echoes associated with the first ultrasound energy; and detect an anatomical feature based on the image data. The processor circuit may be configured to identify the acoustic window further based on the anatomical feature. In some aspects, the processor circuit may be further configured to: determine a measurement associated with an anatomical feature included in the image; and output a graphical representation of the measurement to the display. In some aspects, the measurement includes at least one of a diaphragm excursion measurement, a diaphragm thickness measurement, or a diaphragm thickening fraction. In some aspects, the processor circuit may be further configured to output a graphical representation of a confidence metric associated with the measurement to the display.

In some aspects, the processor circuit may be in communication with a tracking system, and the processor circuit may be configured to determine identify the acoustic window further based on data received from the tracking system. In some aspects, the processor circuit may be further configured to select a beam steering angle from among a plurality of beam steering angles. In such aspects, the processor circuit may be configured to control the array of acoustic elements to transmit the second ultrasound energy further based on the beam steering angle. In some aspects, the processor circuit may be configured to select the beam steering angle based on a comparison of an echogenicity of an anatomical feature associated with the beam steering angle and an echogenicity of the anatomical feature associated with an additional beam steering angle of the plurality of beam steering angles. In some aspects, the processor circuit may be configured to select the beam steering angle further based on identifying a first wall and a second wall of the anatomical feature. In some aspects, the processor circuit may be configured to determine an additional acoustic setting based on the acoustic window. The processor circuit may be configured to control the array of acoustic elements to transmit the second ultrasound energy further based on the additional acoustic setting.

In an exemplary aspect, a method of ultrasound imaging, includes: controlling, by a processor circuit, an array of acoustic elements in communication with the processor circuit to transmit first ultrasound energy at a first frequency and receive echoes associated with the first ultrasound energy; identifying, by the processor circuit, an acoustic window based on the echoes associated with the first ultrasound energy; determining, by the processor circuit, a second frequency based on the acoustic window; controlling, by the processor circuit, the array of acoustic elements to transmit second ultrasound energy at the second frequency and receive echoes associated with the second ultrasound energy; generating, by the processor circuit, an image based on the echoes associated with the second ultrasound energy; and outputting, by the processor circuit, the image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4 is a flow diagram of a method of adaptively controlling an acoustic setting for an ultrasound transmission, according to aspects of the present disclosure.

DETAILED DESCRIPTION

Figure 1:
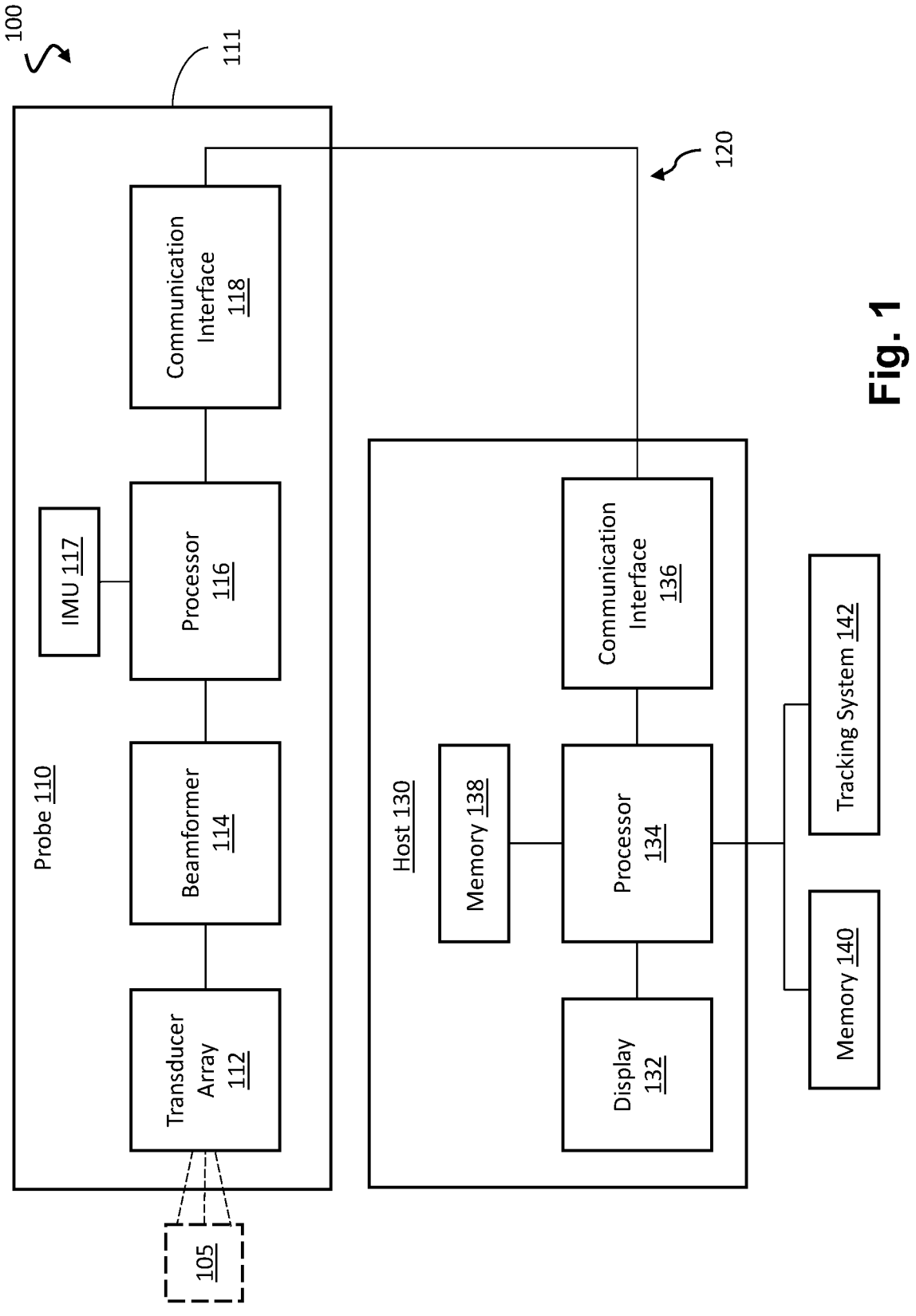
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ultrasound imaging system is described in terms of diaphragm imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 may include a transducer array 112, a beamformer 114, a processor 116, and a communication interface 118. The host 130 may include a display 132, a processor circuit 134, a communication interface 136, and a memory 138 storing patient information. The host 130 and/or the processor 134 of the host 130 may additionally be in communication with a memory 140, and a tracking system 142.

In some embodiments, the probe 110 is an external ultrasound imaging device including a housing 111 configured for handheld operation by a user. The transducer array 112 can be configured to obtain ultrasound data while the user grasps the housing 111 of the probe 110 such that the transducer array 112 is positioned adjacent to or in contact with a patient's skin. The probe 110 is configured to obtain ultrasound data of anatomy within the patient's body while the probe 110 is positioned outside of the patient's body. In some embodiments, the probe 110 can be a patch-based external ultrasound probe.

In other embodiments, the probe 110 can be an internal ultrasound imaging device and may comprise a housing 111 configured to be positioned within a lumen of a patient's body, including the patient's coronary vasculature, peripheral vasculature, esophagus, heart chamber, or other body lumen or body cavity. In some embodiments, the probe 110 may be an intravascular ultrasound (IVUS) imaging catheter or an intracardiac echocardiography (ICE) catheter. In other embodiments, probe 110 may be a transesophageal echocardiography (TEE) probe. Probe 110 may be of any suitable form for any suitable ultrasound imaging application including both external and internal ultrasound imaging.

In some embodiments, aspects of the present disclosure can be implemented with medical images of patients obtained using any suitable medical imaging device and/or modality. Examples of medical images and medical imaging devices include x-ray images (angiographic images, fluoroscopic images, images with or without contrast) obtained by an x-ray imaging device, computed tomography (CT) images obtained by a CT imaging device, positron emission tomography-computed tomography (PET-CT) images obtained by a PET-CT imaging device, magnetic resonance images (MRI) obtained by an MRI device, single-photon emission computed tomography (SPECT) images obtained by a SPECT imaging device, optical coherence tomography (OCT) images obtained by an OCT imaging device, and intravascular photoacoustic (IVPA) images obtained by an IVPA imaging device. The medical imaging device can obtain the medical images while positioned outside the patient body, spaced from the patient body, adjacent to the patient body, in contact with the patient body, and/or inside the patient body.

For an ultrasound imaging device, the transducer array 112 emits ultrasound signals towards an anatomical object 105 of a patient and receives echo signals reflected from the object 105 back to the transducer array 112. The transducer array 112 can include any suitable number of acoustic elements, including one or more acoustic elements and/or a plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 112 can be configured to obtain one-dimensional, two-dimensional, and/or three-dimensional images of a patient's anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

Further, in some embodiments, the transducer array 112 may be a broadband transducer array. That is, for example, the transducer array 112 may be configured to transmit ultrasound energy over a range of frequency. As an illustrative example, the transducer array may be configured to transmit ultrasound energy at a frequency between 2 megahertz (MHz) and 12 MHz. For instance, for some ultrasound imaging applications, the transducer array 112 may be used to transmit ultrasound energy at a relatively low frequency (e.g., 2-4 MHz), while the transducer array 112 may be used for other imaging applications to transmit ultrasound energy at a relatively high frequency (e.g., 8-12 MHz). In particular, the transducer array 112 may be used to transmit ultrasound energy at a higher frequency to image features at a shallower depth, such as a zone of apposition of a diaphragm, and the transducer array 112 may be used to transmit ultrasound energy at a lower frequency to image features at greater depths, such as a zone of dome of a diaphragm, as described in greater detail below.

The object 105 may include any anatomy or anatomical feature, such as a diaphragm, blood vessels, nerve fibers, airways, mitral leaflets, cardiac structure, abdominal tissue structure, appendix, large intestine (or colon), small intestine, kidney, liver, and/or any other anatomy of a patient. In some aspects, the object 105 may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object 105 may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. In some embodiments, the beamformer 114 may apply a time-delay to signals sent to individual acoustic transducers within an array in the transducer array 112 such that an acoustic signal is steered in any suitable direction propagating away from the probe 110. The beamformer 114 may further provide image signals to the processor 116 based on the response of the received ultrasound echo signals. The beamformer 114 may include multiple stages of beamforming. The beamforming can reduce the number of signal lines for coupling to the processor 116. In some embodiments, the transducer array 112 in combination with the beamformer 114 may be referred to as an ultrasound imaging component.

The processor 116 is coupled to the beamformer 114. The processor 116 may also be described as a processor circuit, which can include other components in communication with the processor 116, such as a memory, beamformer 114, communication interface 118, and/or other suitable components. The processor 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor 116 may also be implemented as a combination of computing devices, e.g., a combination of a DSP and a microprocessor, a plurality of microprocessors, one or more microprocessors in conjunction with a DSP core, or any other such configuration. The processor 116 is configured to process the beamformed image signals. For example, the processor 116 may perform filtering and/or quadrature demodulation to condition the image signals. The processor 116 and/or 134 can be configured to control the array 112 to obtain ultrasound data associated with the object 105.

The probe 110 can include an inertial measurement unit (IMU) 117, which is an electronic device that generates IMU data (e.g., specific force, angular rate, orientation, proper acceleration, angular velocity, etc.). The IMU 117 can include one or more accelerometers, gyroscopes, and/or magnetometers disposed within the housing 111 of the probe 110. The IMU data can be representative of the probe 110 during operation of the probe 110 to acquire ultrasound images.

The communication interface 118 is coupled to the processor 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor 134 is coupled to the communication interface 136. The processor 134 may also be described as a processor circuit, which can include other components in communication with the processor 134, such as the memory 138, the communication interface 136, and/or other suitable components. The processor 134 may be implemented as a combination of software components and hardware components. The processor 134 may include a central processing unit (CPU), a graphics processing unit (GPU), a digital signal processor (DSP), an application-specific integrated circuit (ASIC), a controller, an FPGA device, another hardware device, a firmware device, or any combination thereof configured to perform the operations described herein. The processor 134 may also be implemented as a combination of computing devices, e.g., a combination of a DSP and a microprocessor, a plurality of microprocessors, one or more microprocessors in conjunction with a DSP core, or any other such configuration. The processor 134 can be configured to generate image data from the image signals received from the probe 110. The processor 134 can apply advanced signal processing and/or image processing techniques to the image signals. An example of image processing includes conducting a pixel level analysis to evaluate whether there is a change in the color of a pixel, which may correspond to an edge of an object (e.g., the edge of an anatomical feature). In some embodiments, the processor 134 can form a three-dimensional (3D) volume image from the image data. In some embodiments, the processor 134 can perform real-time processing on the image data to provide a streaming video of ultrasound images of the object 105.

The memory 138 is coupled to the processor 134. The memory 138 may be any suitable storage device, such as a cache memory (e.g., a cache memory of the processor 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory.

The memory 138 can be configured to store patient information, measurements, data, or files relating to a patient's medical history, history of procedures performed, anatomical or biological features, characteristics, or medical conditions associated with a patient, computer readable instructions, such as code, software, or other application, as well as any other suitable information or data. The memory 138 may be located within the host 130. Patient information may include measurements, data, files, other forms of medical history, such as but not limited to ultrasound images, ultrasound videos, and/or any imaging information relating to the patient's anatomy. The patient information may include parameters related to an imaging procedure such as an acoustic window and/or a probe position and/or orientation. The patient information may include data, images, metrics, or other information related to the tracking system 142 and/or the IMU 117. The memory 138 can also be configured to store information related to the training and implementation of deep learning networks (e.g., neural networks). Mechanisms for training and implementing the deep learning networks are described in greater detail herein.

Any or all of the previously mentioned computer readable media, such as patient information, code, software, or other applications, or any other suitable information or data may also be stored the memory 140. The memory 140 may serve a substantially similar purpose to the memory 138 but may not be located within the host 130. For example, in some embodiments, the memory may be a cloud-based server, an external storage device, or any other device for memory storage. The host 130 may be in communication with the memory 140 by any suitable means as described. The host 130 may be in communication with the memory 140 continuously or they may be in communication intermittently upon the request of the host 130 or a user of the ultrasound system 100.

The processor 134 of the host 130 may also be in communication with a tracking system 142. The tracking system 142 may track the position and/or orientation of the probe 110. For instance, the tracking system 142 may locate the position of the probe 110 with respect to a patient's anatomy. In some embodiments, for example, the tracking system 142 may include a camera or imaging system positioned to image the probe 110 as the probe 110 is controlled to obtain an ultrasound image. The tracking system 142 and/or the processor 134 may thus determine the position and/or orientation (e.g., angle) of the probe 110 relative to the patient based on analysis of one or more images of the probe 110 captured at the tracking system 142. Additionally or alternatively, the tracking system 142 may include magnetometers configured to detect the position and/or orientation of the probe 110 based on a magnetic field of the probe 110. The host 130 may be in communication with the tracking system 142 by any suitable means as described. The host 130 may be in communication with the tracking system 142 continuously or they may be in communication intermittently upon the request of the host 130 or a user of the ultrasound system 100.

The host 130 may be in communication with the memory 140 and/or the tracking system 142 via any suitable communication method. For example, the host 130 may be in communication with the memory 140 and/or the tracking system 142 via a wired link, such as a USB link or an Ethernet link. Alternatively, the host 130 may be in communication with the memory 140 and/or the tracking system 142 via a wireless link, such as an UWB link, an IEEE 802.11 WiFi link, or a Bluetooth link. The display 132 is coupled to the processor circuit 134. The display 132 may be a monitor or any suitable display. The display 132 is configured to display the ultrasound images, image videos, and/or any imaging information of the object 105.

The system 100 may be used to assist a sonographer in performing an ultrasound scan. The scan may be performed in a point-of-care setting. In some instances, the host 130 is a console or movable cart. In some instances, the host 130 may be a mobile device, such as a tablet, a mobile phone, or portable computer. During an imaging procedure, the ultrasound system 100 can acquire an ultrasound image of a region of interest within a patient's anatomy. In particular, the ultrasound system 100 may acquire ultrasound images of a zone of apposition of a diaphragm and/or a zone of dome of the diaphragm. More specifically, the ultrasound system 100 may be configured to identify an anatomical feature, such as the zone of dome or the zone of apposition, and/or an acoustic window and to set or adjust a frequency used for an ultrasound transmission based on the identification. For instance, because the zone of apposition may be positioned at a relatively shallower depth from the probe 110 than the zone of dome, the zone of apposition may be imaged at a relatively higher frequency than the zone of dome. Thus, based on identifying the zone of apposition, the ultrasound system 100 may be configured to set a frequency of ultrasound energy transmitted at the probe 110 to a relatively higher frequency, and based on identifying the zone of dome, the ultrasound system 100 may be configured to set the frequency to a relatively lower frequency.

In some embodiments, the ultrasound system 100 may identify the zone of apposition or the zone of dome based on ultrasound image data associated with an ultrasound transmission corresponding to a first frequency (e.g., a predetermined and/or a default frequency). For instance, the ultrasound system 100 may analyze the ultrasound image data to identify various parameters, such as anatomical features (e.g., the presence of particular tissues and/or organs within the image data), an orientation and/or a position of the probe 110, a depth setting associated with the ultrasound transmission, a user input, and/or the like, that may distinguish the ultrasound image data as corresponding to the zone of dome or the zone of apposition.

In some aspects, the processor 134 may utilize deep learning-based prediction networks to identify parameters of an ultrasound image, including an acoustic window, probe orientation, patient position, and/or other parameters. In some aspects, the processor 134 may receive metrics or perform various calculations relating to the region of interest imaged during an imaging procedure. These metrics and/or calculations may also be displayed to the sonographer or other user via the display 132. For instance, the processor 134 may receive or determine a confidence metric associated with the identification of an anatomical feature and/or an acoustic window, which may be output to the display 132. Additionally or alternatively, the processor 134 may receive or determine measurements associated with a diaphragm of a patient, such as a diaphragm thickness measurement and/or a diaphragm excursion measurement. The processor 134 may further determine a confidence metric associated with the measurements, and any of the measurements or the confidence metric associated with the measurements may be output to the display 132.

Figure 2:
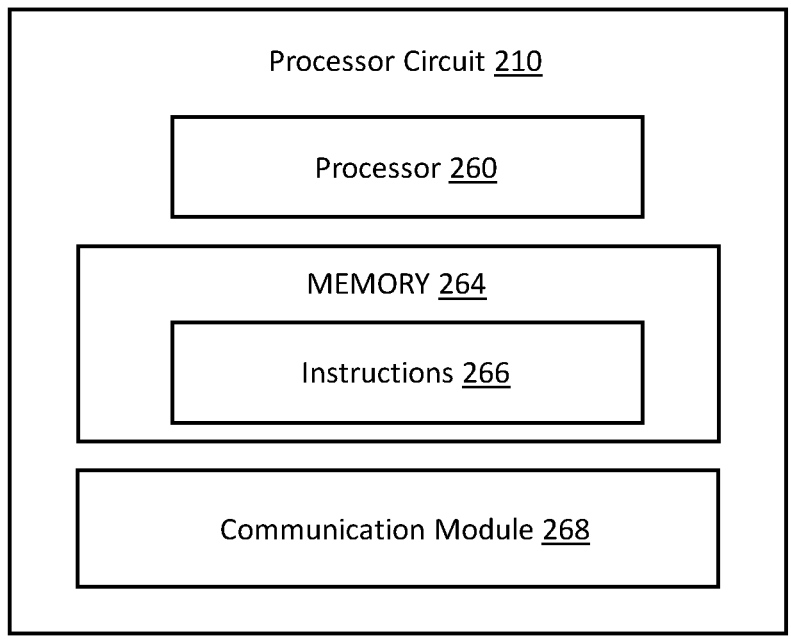
FIG. 2 is a schematic diagram of a processor circuit, according to aspects of the present disclosure.

FIG. 2 is a schematic diagram of a processor circuit, according to aspects of the present disclosure. The processor circuit 210 may be implemented in the probe 110, the host system 130 of FIG. 1, or any other suitable location. One or more processor circuits can be configured to carry out the operations described herein. The processor circuit 210 can be part of the circuitry 116 and/or circuitry 134 or may be separate circuitry. In an example, the processor circuit 210 may be in communication with the transducer array 112, beamformer 114, communication interface 118, communication interface 136, IMU 117, memory 138, memory 140, tracking system 142, and/or the display 132, as well as any other suitable component or circuit within ultrasound system 100. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration. The processor 260 may also implement various deep learning networks, which may include a hardware or a software implementation. The processor 260 may additionally include a preprocessor in either hardware or software implementation.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 760, cause the processor 260 to perform the operations described herein with reference to the probe 110 and/or the host 130 (FIG. 1). Instructions 266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements. Instructions 266 may include various aspects of a deep learning network, such as a convolutional neural network (CNN), or various other instructions or code.

The communication module 268 can include any electronic circuitry and/or logic circuitry to facilitate direct or indirect communication of data between the processor circuit 210, the probe 110, and/or the display 132. In that regard, the communication module 268 can be an input/output (I/O) device. In some instances, the communication module 268 facilitates direct or indirect communication between various elements of the processor circuit 210 and/or the probe 110 (FIG. 1) and/or the host 130 (FIG. 1).

Figure 3:
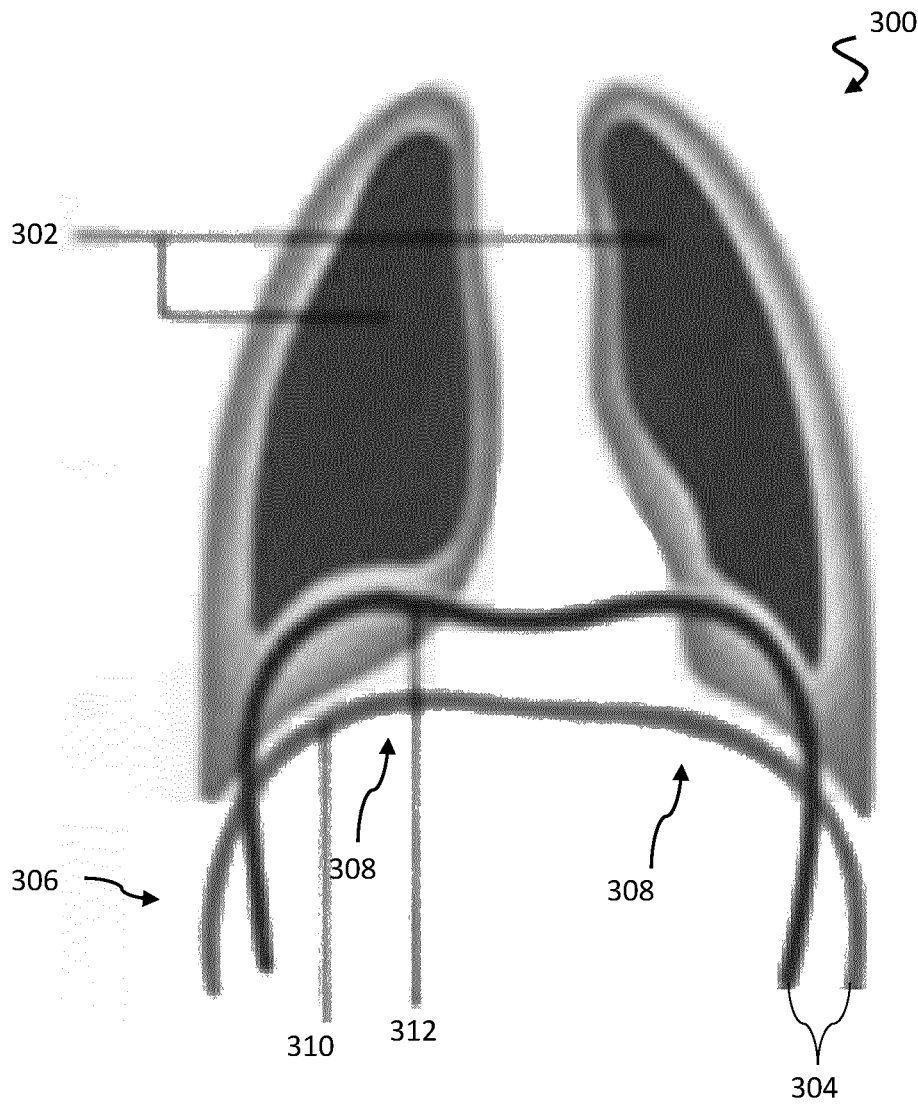
FIG. 3 is a schematic diagram of an anatomy, according to aspects of the present disclosure.

FIG. 3 is a diagram of an anatomy 300 of a patient, which may be a target of ultrasound imaging, in accordance with the present disclosure. In particular, FIG. 3 illustrates the anatomy of lungs 302 and a diaphragm 304, as well as the position of the diaphragm 304, during a respiratory cycle. The respiratory cycle may begin with the patient intaking a breath (e.g., inspiration) and may end with the patient exhaling (e.g., expiration) or vice versa. As illustrated, the diaphragm, which includes a zone of apposition 306 and a zone of dome 308, may reside in a first position 310 at inspiration and may transition to a second position 312 to facilitate expiration.

Imaging the zone of apposition 306 or the zone of dome 308 may involve accounting for and/or adapting to the change of position of the zone of apposition 306 or the zone of dome 308 at different points within the respiratory cycle. That is, for example, characteristics, such as the depth, echogenicity, angle, and/or the like, of the zone of dome 308 and/or the zone of apposition 306 may change over the respiratory cycle. As such, tuning one or more acoustic settings used for ultrasound imaging, such as a frequency, a beam steering angle, a focal depth (e.g., a depth-dependent focus), a gain, an imaging profile (e.g., trapezoid imaging), and/or the like over the respiratory cycle and/or at a certain point of the respiratory cycle may improve the image quality of the resulting image (e.g., in comparison with images resulting from relatively constant acoustic settings over the respiratory cycle). As further shown, the zone of dome 308 and the zone of apposition 306 are located at different positions (e.g., proximate to different anatomies). To that end, the zone of dome 308 may be imaged at a relatively greater depth than the zone of apposition 306. As such, ultrasound imaging of the zone of dome 308 at a relatively low frequency may produce an image with improved penetration in comparison with an image of the zone of dome 308 acquired based on a relatively high frequency. Similarly, ultrasound imaging of the zone of apposition 306 at a relatively high frequency may produce an image with improved resolution in comparison with an image of the zone of apposition 306 acquired based on a relatively low frequency. Mechanisms of adaptively controlling one or more acoustic settings for imaging (e.g., ultrasound imaging) the zone of dome 308 and the zone of apposition 306 and/or for imaging the diaphragm 304 over a respiratory cycle are described herein. However, while embodiments described herein relate to the imaging of the diaphragm, embodiments are not limited thereto. Instead, the adaptive control of one or more acoustic settings described herein may be applied to any suitable set of anatomical features or regions of interest.

FIG. 4 is a flow diagram of a method 400 of adaptively controlling an acoustic setting (e.g., a frequency) used for an ultrasound transmission based on an anatomical feature (e.g., a zone of dome or a zone of apposition) being imaged, according to aspects of the present disclosure. As illustrated, the method 400 includes a number of enumerated steps, but embodiments of the method 400 may include additional steps before, after, or in between the enumerated steps. In some embodiments, one or more of the enumerated steps may be omitted, performed in a different order, or performed concurrently. The steps of the method 400 can be carried out by any suitable component within the ultrasound imaging system 100 and all steps need not be carried out by the same component. In some embodiments, one or more steps of the method 400 can be performed by, or at the direction of, a processor circuit of the ultrasound imaging system 100, including, e.g., the processor 260 (FIG. 2) or any other component.

At step 402, the method 400 includes controlling an array of acoustic elements to transmit first ultrasound energy at a first frequency and receive echoes associated with the first ultrasound energy. In some embodiments, for example, the ultrasound imaging system 100 may control the transducer array 112 of the probe 110 to transmit the first ultrasound energy at the first frequency. For instance, the host 130 may transmit a transmit pulse pattern to the probe 110 based on the first frequency, and using the transmit pulse pattern, the probe 110 may transmit the first ultrasound energy at the first frequency.

In some embodiments, the first frequency may be a predetermined and/or preconfigured frequency. For instance, the first frequency may be stored at the host 130 (e.g., at memory 138). As an illustrative example, the first frequency may be between a minimum and a maximum ultrasound transmission frequency producible at the array of acoustic elements. For an ultrasound probe (e.g., probe 110) and/or a transducer array configured to transmit ultrasound energy at a frequency between 2 MHz and 10 MHz, the first frequency may be 5 MHz, for example.

At step 404, the method 400 may involve identifying an acoustic window based on the echoes associated with the first ultrasound energy. The acoustic window may correspond to a position of an ultrasound probe (e.g., probe 110) on the patient's body, a region being imaged by the first ultrasound energy, and/or the like. For instance, the acoustic window may be associated with a subcostal imaging, which corresponds to a probe positioned below a patient's ribs (e.g., at the base of the ribcage), or intercostal imaging, which corresponds to a probe positioned along and/or between the patient's ribs (e.g., between two ribs of the patient). Additionally or alternatively, the acoustic window may be associated with an anatomical feature imaged by the first ultrasound energy. More specifically, the acoustic window may be associated with a target anatomical feature (e.g., a region of interest), such as the zone of apposition or the zone of dome of a diaphragm. Moreover, in some embodiments, the acoustic window may be associated with an anatomical feature in proximity to the target anatomical feature. With respect to the zone of apposition, for example, the region imaged by the first ultrasound energy may include a portion of the patient's lung and/or muscle tissue, such as intercostal muscle tissue. With respect to the zone of dome, the region imaged by the first ultrasound energy may include a portion of the patient's liver. An acoustic window corresponding to the zone of dome of a diaphragm is described in further detail with respect to FIGS. 5A-B, and an acoustic window corresponding to the zone of apposition of the diaphragm is described in further detail with respect to FIGS. 6A-B.

Figure 5A:
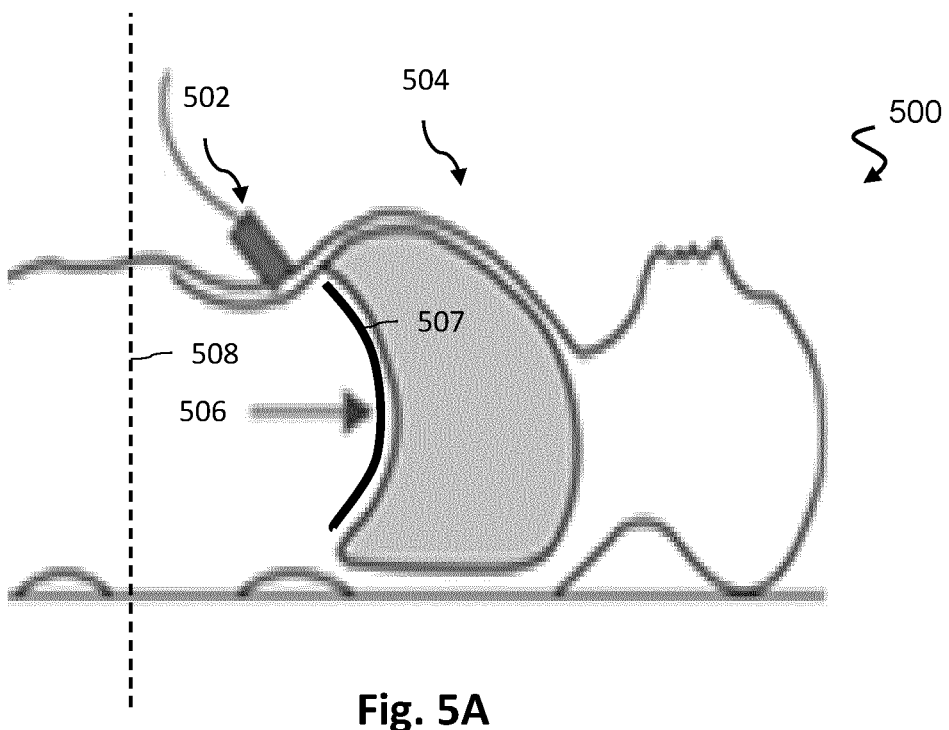
FIG. 5A is a diagrammatic view of subcostal imaging, according to aspects of the present disclosure.
Figure 5B:
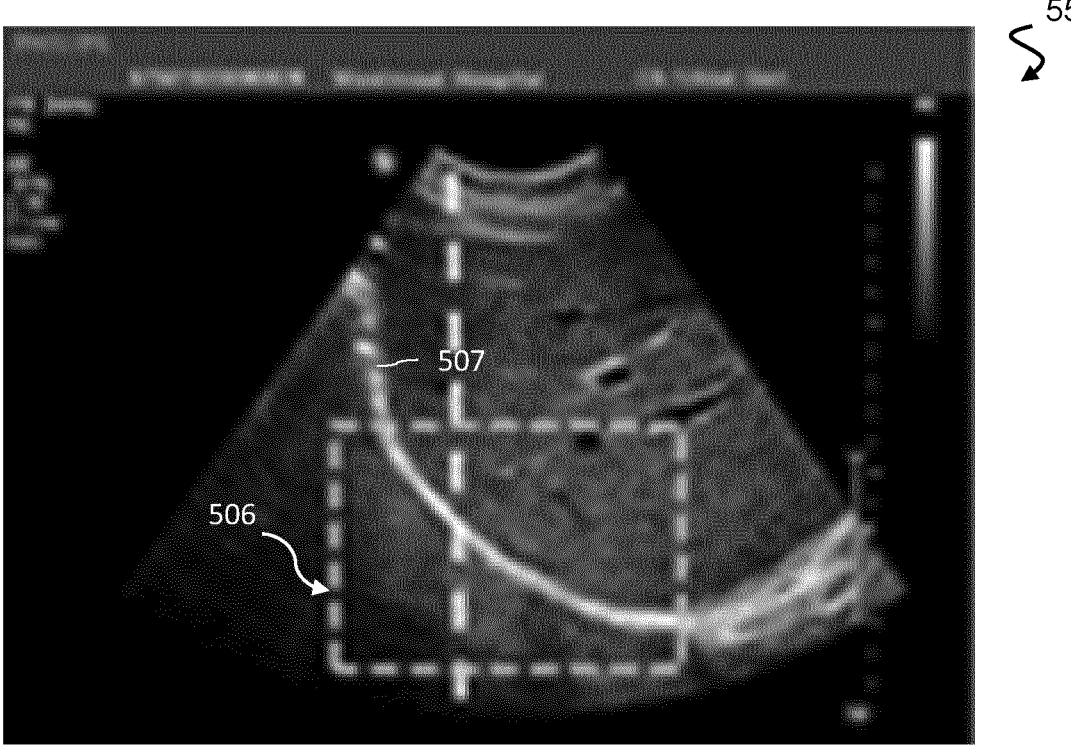
FIG. 5B is a diagrammatic view of an ultrasound image, according to aspects of the present disclosure.

FIG. 5A illustrates a schematic diagram 500 of subcostal imaging, which may be used to produce the ultrasound image 550 illustrated in FIG. 5B. In particular, FIG. 5A provides an example of a position of an ultrasound probe 502, which may be substantially similar to the probe 110, relative to a patient 504 for imaging of the zone of dome 506 of the patient's diaphragm 507. That is, for example, FIG. 5A illustrates an ultrasound positioning that may correspond to an acoustic window associated with the zone of dome 506. As illustrated, the ultrasound probe 502 may be positioned in a subcostal region (e.g., below the patient's ribcage) on the patient's anterior (e.g., ventral) side. Moreover, the probe 502 may be oriented at an angle relative to a lateral axis 508 to image the zone of dome 506. Additionally or alternatively, ultrasound energy may be transmitted at an angle from the ultrasound probe 502 via beam steering to image the zone of dome 506, as described in greater detail below.

FIG. 5B is an illustrative example of an ultrasound image 550 of the zone of dome 506. To that end, the ultrasound image 550 may correspond to an acoustic window associated with the zone of dome 506.

Figure 6A:
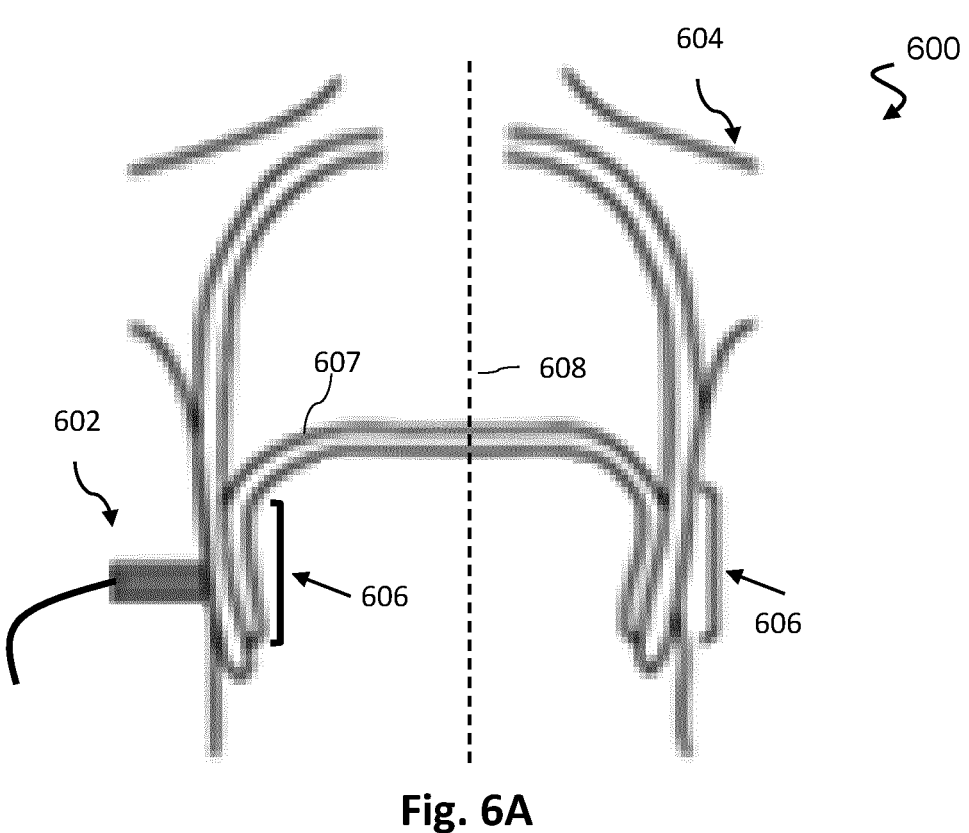
FIG. 6A is a diagrammatic view of intercostal imaging, according to aspects of the present disclosure.
Figure 6B:
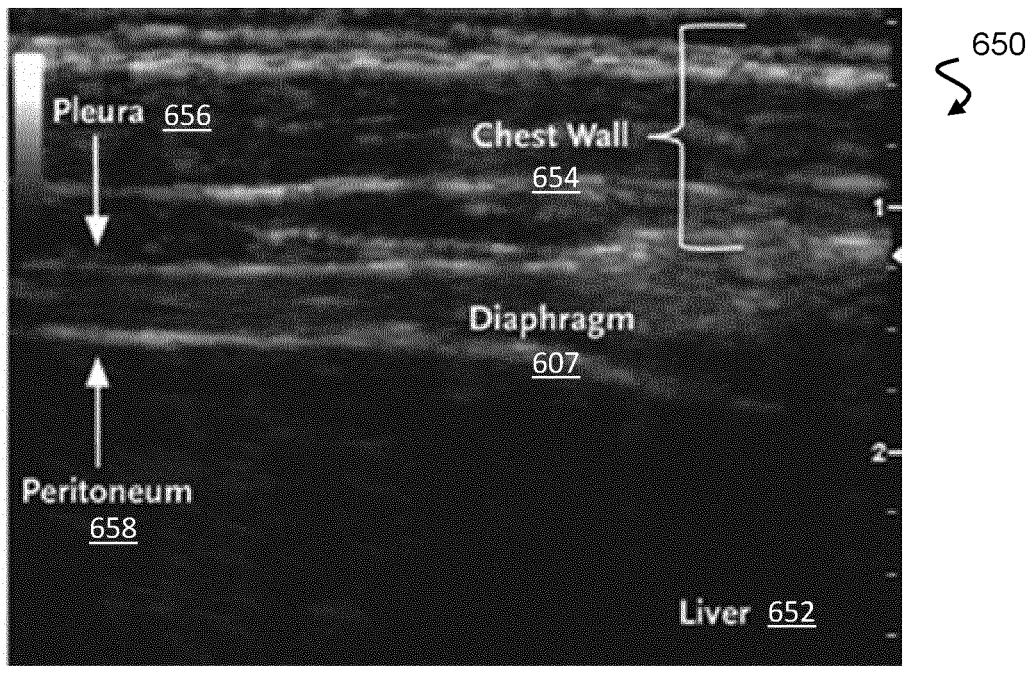
FIG. 6B is a diagrammatic view of an ultrasound image, according to aspects of the present disclosure.

FIG. 6A illustrates a schematic diagram 600 of intercostal imaging, which may be used to produce the ultrasound image 650 illustrated in FIG. 6B. In particular, FIG. 6A provides an example of a position of an ultrasound probe 602, which may be substantially similar to the probe 110, relative to a patient 604 for imaging of the zone of apposition 606 of the patient's diaphragm 607. That is, for example, FIG. 6A illustrates an ultrasound positioning that may correspond to an acoustic window associated with the zone of apposition 606. As illustrated, the ultrasound probe 602 may be positioned in an intercostal region (e.g., along the patient's ribcage) on the patient's right side. As such, the zone of apposition 606 may be imaged through (e.g., with respect to) a liver window. As further illustrated, the diaphragm includes a zone of apposition 606 on both the patient's right and left side. Thus, while the illustrated embodiment is described with respect to the ultrasound probe 602 being positioned on the patient's right side, the probe 602 may additionally or alternatively be positioned on the patient's left side. In such cases, the zone of apposition 606 may be imaged through a spleen window.

In some embodiments, the probe 602 may be oriented relatively perpendicular to a longitudinal axis 608 to image the zone of apposition 606. However, embodiments are not limited thereto. Instead, any suitable angle of offset with respect to the longitudinal axis 608 may be employed to image the zone of apposition. Additionally or alternatively, ultrasound energy may be transmitted at an angle from the ultrasound probe 602 via beam steering to image the zone of apposition 606, as described in greater detail below.

FIG. 6B is an illustrative example of an ultrasound image 650 of the zone of apposition 606. To that end, the ultrasound image 650 may correspond to an acoustic window associated with the zone of apposition 606. As illustrated, an ultrasound image of the zone of apposition 606 may include a portion of the patient's liver 652. The image may further include a portion of the patient's chest wall 654, such as the patient's intercostal muscle and/or a rib of the patient. As further show, the diaphragm 607 may include a pleura 656 (e.g., a parietal pleura), as well as a peritoneum layer 658.

Returning now to FIG. 4, identifying the acoustic window (e.g., at step 404) may involve analysis of image data generated based on the echoes associated with the first ultrasound energy. For instance, in some embodiments, the ultrasound imaging system 100 may receive signals based on the echoes associated with the first ultrasound energy and may determine the image data based on the signals. For example, the probe 110 may generate the image data based on the echoes at the processor 116, for example, and may transmit the image data to the host 130 for analysis. Based on the image data, the host 130 and/or the ultrasound imaging system 100 may identify the acoustic window. In particular, the host 130 may determine whether the acoustic window corresponds to the zone of dome, such as the acoustic window resulting from the ultrasound probe position illustrated in FIG. 5A and/or the ultrasound image depicted in FIG. 5B, or the acoustic window corresponds to the zone of apposition, such as the acoustic window resulting from the ultrasound probe position illustrated in FIG. 6A and/or the ultrasound image depicted in FIG. 6B.

For instance, in some embodiments, the host 130 and/or the ultrasound imaging system 100 may employ a deep learning network to classify and/or identify the acoustic window based on the acquired ultrasound image data. In some embodiments, the deep learning network may be a convolutional neural network (CNN) or another appropriate neural network. In other embodiments, the deep learning network may be any other suitable implementation of an artificial intelligence and/or machine learning system or structure including, for example, a random forest deep learning approach, a regression analysis approach, or any other suitable approach or structure. The deep learning network is trained prior to the initiation of the method 400 to identify an acoustic window associated with a given ultrasound image. As such, the ultrasound imaging system may use the deep learning network to analyze the content of the acquired ultrasound image and determine the acoustic window from the image itself and the anatomical landmarks present in the field of view. Additionally or alternatively, the deep learning network may use data corresponding to the orientation and/or position of the ultrasound probe (e.g., probe 110), such as IMU orientation data and/or data from the tracking system 142, to determine the acoustic window. Further, in some embodiments, a user can provide an initial input (e.g., via the host 130) regarding the expected location of the imaging window, and the deep learning network may determine a prediction and confidence score with respect to the current the acoustic window. Details of the deep learning network and the training of the deep learning network are discussed with reference to FIG. 8 below.

At step 406, the method 400 includes determining a second frequency based on the acoustic window. In particular, the second frequency may be determined based on whether the acoustic window corresponds to the zone of dome or the zone of apposition. For instance, the host 130 may be configured with a mapping between an acoustic window corresponding to the zone of dome and frequencies suitable for imaging the zone of dome, as well as a mapping between an acoustic window corresponding to the zone of apposition and frequencies suitable for imaging the zone of apposition. To that end, based on identifying the acoustic window as an acoustic window corresponding to the zone of dome, the host 130 may set the second frequency between 2-4 MHz, and based on identifying the acoustic window as an acoustic window corresponding to the zone of apposition, the host 130 may set the second frequency between 8-12 MHz.

In some cases, the acoustic window identified at step 404 may not correspond to the zone or dome or the zone of apposition. For instance, a sonographer may place the probe 110 in a position and/or at an orientation (e.g., with respect to the longitudinal axis 608 and the lateral axis 508) offset from the positions and/or orientations suitable for capturing an ultrasound image of the zone of dome and/or the zone of apposition. In particular, the acoustic window may be identified as epigastric, lateral, parasagittal, flank, or another suitable acoustic window. In such cases, the host 130 may output an indication to the display 132 that an image of the zone of dome and/or the zone of apposition has not been captured. That is, for example, the host 130 may output a graphical representation, such as an icon, text, and/or the like to the display 132. The graphical representation may further alert the sonographer to adjust the placement and/or orientation of the probe 110 to capture an image of the zone of dome and/or the zone of apposition. Further, after the probe 110 is repositioned and/or reoriented, the host 130 may control the transducer array 112 to once again transmit ultrasound energy at the first frequency and receive echoes associated with the ultrasound energy (e.g., step 402). The host 130 may then identify the acoustic window corresponding to the updated probe position (e.g., step 406). In this way, the host 130 may repeat one or more steps of the method 400 (e.g., step 402 and step 404) until an acoustic window corresponding to the zone of dome or the zone of apposition is identified (e.g., at step 404). Thus, in some embodiments, the host 130 may determine the second frequency for imaging the zone of apposition or the zone of dome at step 406, as described above.

At step 408, the method 400 involves controlling the array of acoustic elements to transmit second ultrasound energy at the second frequency and receive echoes associated with the second ultrasound energy. That is, for example, the host 130 may control the array of acoustic elements (e.g., the transducer array 112) based on the acoustic window being identified as corresponding to the zone of dome or the zone of apposition. For instance, for an acoustic window identified as corresponding to the zone of apposition, the host 130 may control the transducer array 112 to transmit the second ultrasound energy at a relatively higher frequency, while for an acoustic window identified as corresponding to the zone of dome, the host 130 may control the array of acoustic elements to transmit the second ultrasound energy at a relatively lower frequency.

At step 410, the method 400 includes generating an image based on echoes associated with the second ultrasound energy. In some embodiments, the probe 110 may generate image data based on the received echoes at the beamformer 114 and/or the processor 116, for example, and may transmit the image data to the host 130. To that end, the host 130 may receive signals based on the echoes, such as image data received from the probe 110, and may generate the image based on the signals. In particular, the processor 134 can be configured to generate image data from the image signals received from the probe 110. The processor 134 can apply advanced signal processing and/or image processing techniques to the image signals.

Because the second frequency may be selected based on the identified acoustic window, the resolution and/or penetration of the generated image may be greater than the resolution and/or penetration of the image data and/or image corresponding to the received echoes associated with the first ultrasound energy (e.g., at step 402). That is, for example, the host 130 may be configured to optimize the frequency used for imaging the identified acoustic window. For instance, the image may be generated based on a relatively higher frequency for the zone of apposition and a relatively lower frequency for the zone of dome, as described herein. As a result, the second frequency may differ from the first frequency, which may improve the resolution of the generated image and/or the penetration of the generated image.

At step 412, the method 400 may involve outputting the generated image to display. For example, the host 130 may output the image to the display 132.

As described herein, the ultrasound imaging system 100 may set and/or adjust the frequency used for ultrasound imaging based on the acoustic window. For instance, the ultrasound imaging system 100 may tune the frequency used to transmit ultrasound energy at the probe 110 to image the zone of apposition or the zone of dome of a diaphragm with a certain image quality (e.g., resolution and/or penetration). In this way, the ultrasound imaging system 100 may adjust an acoustic setting associated with acquiring and/or generating an ultrasound image. Moreover, the ultrasound imaging system 100 may additionally or alternatively adjust and/or select an additional acoustic setting associated with the acquisition and/or generation of the ultrasound image, such as a beam steering angle, a focal depth (e.g., a depth-dependent focus), a gain, an imaging profile (e.g., trapezoid imaging), and/or the like. As such, the ultrasound imaging system 100 may further optimize the resulting image quality of the generated image, as described in greater detail below.

Figure 7:
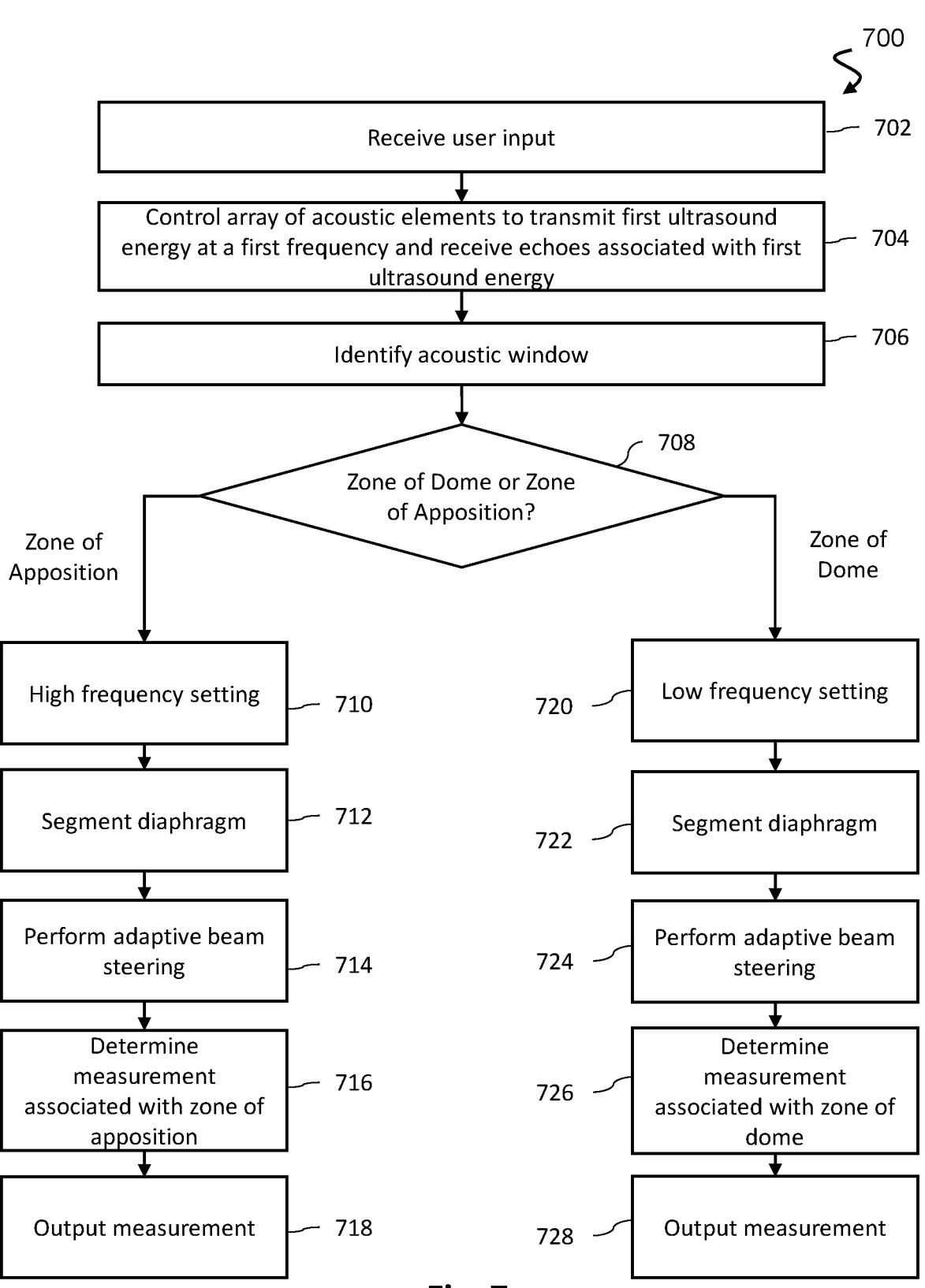
FIG. 7 is a flow diagram of a method of adaptively controlling an acoustic setting for an ultrasound transmission, according to aspects of the present disclosure.

With reference now to FIG. 7, a flow diagram of a method 700 of adaptively controlling the acoustic settings, such as the frequency and/or the beam steering angle, used for an ultrasound transmission based on an anatomical feature (e.g., a zone of dome or a zone of apposition) being imaged, according to aspects of the present disclosure. As illustrated, the method 700 includes a number of enumerated steps, but embodiments of the method 700 may include additional steps before, after, or in between the enumerated steps. In some embodiments, one or more of the enumerated steps may be omitted, performed in a different order, or performed concurrently. The steps of the method 700 can be carried out by any suitable component within the ultrasound imaging system 100 and all steps need not be carried out by the same component. In some embodiments, one or more steps of the method 700 can be performed by, or at the direction of, a processor circuit of the ultrasound imaging system 100, including, e.g., the processor 260 (FIG. 2) or any other component.

At step 702, the method 700 involves receiving a user input. In some embodiments, for example, the ultrasound imaging system 100 may receive the user input via the host 130. In particular, the user input may be received via an I/O device, such as the communication module 268. Examples of an I/O device for receiving the user input may include a mouse, a keyboard, a joystick, a scroll wheel, a trackpad, a touch screen display, a button, and/or the like. Further, in some embodiments the ultrasound imaging system 100 may receive the user input via an interaction with a graphical user interface (GUI), which may be provided at the display 132.

In some embodiments, the user input may correspond to a depth setting (e.g., an indication of a spatial extent of a resulting image) for the transmission of ultrasound energy from the probe 110. For instance, a sonographer may select a desired depth (e.g., according to an arbitrary unit) to image a region of interest and/or a particular anatomical feature. As an illustrative example, the depth setting for imaging the zone of dome of a patient's diaphragm may be relatively greater than the depth setting for imaging the zone of apposition of the patient's diaphragm. In particular, the depth setting for imaging the zone of dome may be within the range of 4-16 centimeters (cm), while the depth setting for imaging the zone of apposition may be within the range of 2-4 cm.

In some embodiments, the user input may correspond to a target anatomical feature (e.g., a region of interest) for ultrasound imaging. For instance, the user input may correspond to the selection of the zone of dome or the zone of apposition. The selection of an anatomical feature may be received via a drop-down selection, a button corresponding to the anatomical feature, and/or the like provided at a GUI and/or at the host 130, for example. Additionally or alternatively, the user input may correspond to a designation of an ultrasound position and/or orientation with respect to the patient. As an illustrative example, a two-dimensional and/or three-dimensional outline of a human anatomy or a portion thereof may be provided at a GUI (e.g., at the display 132) to facilitate the designation of the ultrasound probe position. For imaging of the zone of dome, for example, the user input may designate the ultrasound probe position within a subcostal portion of the anatomical outline, while for imaging of the zone of apposition, the user input may designate the ultrasound probe position within an intercostal portion of the anatomical outline.

In some embodiments, the user input may correspond to the selection of a type of ultrasound probe used for an ultrasound imaging operation. For instance, different ultrasound probes compatible with the host 130 may be implemented with different capabilities and/or structures. A probe may be linear or curvilinear, for example, and the range of frequencies that may be used to transmit ultrasound energy may vary from probe to probe. Thus, the user input may correspond to a selection of a particular probe from a list of probes compatible with the host 130. Additionally or alternatively, the user input may correspond to a coupling of the ultrasound probe (e.g., probe 110) to the host 130 (e.g., via the communication interface 118 and/or the communication interface 136). In such cases, the host 130 may determine the characteristics and/or capabilities of the probe.

At step 704, the method 700 involves controlling an array of acoustic elements to transmit first ultrasound energy at a first frequency and receive echoes associated with the first ultrasound energy. For instance, as described with reference to step 402 of FIG. 4, the ultrasound imaging system 100 may control the transducer array 112 (e.g., via the host 130 and/or the probe 110) to transmit the first ultrasound energy based on a transmit pulse pattern. As further described, the first frequency may be a predetermined and/or a preconfigured frequency, such as 5 MHz.

At step 706, the method 700 includes identifying an acoustic window. In particular, the ultrasound imaging system 100 may identify the acoustic window associated with the received echoes associated with the first ultrasound energy. In some embodiments, the ultrasound imaging system 100 may identify the acoustic window based on a number of factors, such as the user input, information (e.g., anatomical features) included in an image and/or image data generated based on the received echoes, the orientation and/or position of the probe 110. In particular the ultrasound imaging system 100 may employ a deep learning network to identify the acoustic window based on the one or more of the factors.

Figure 8:
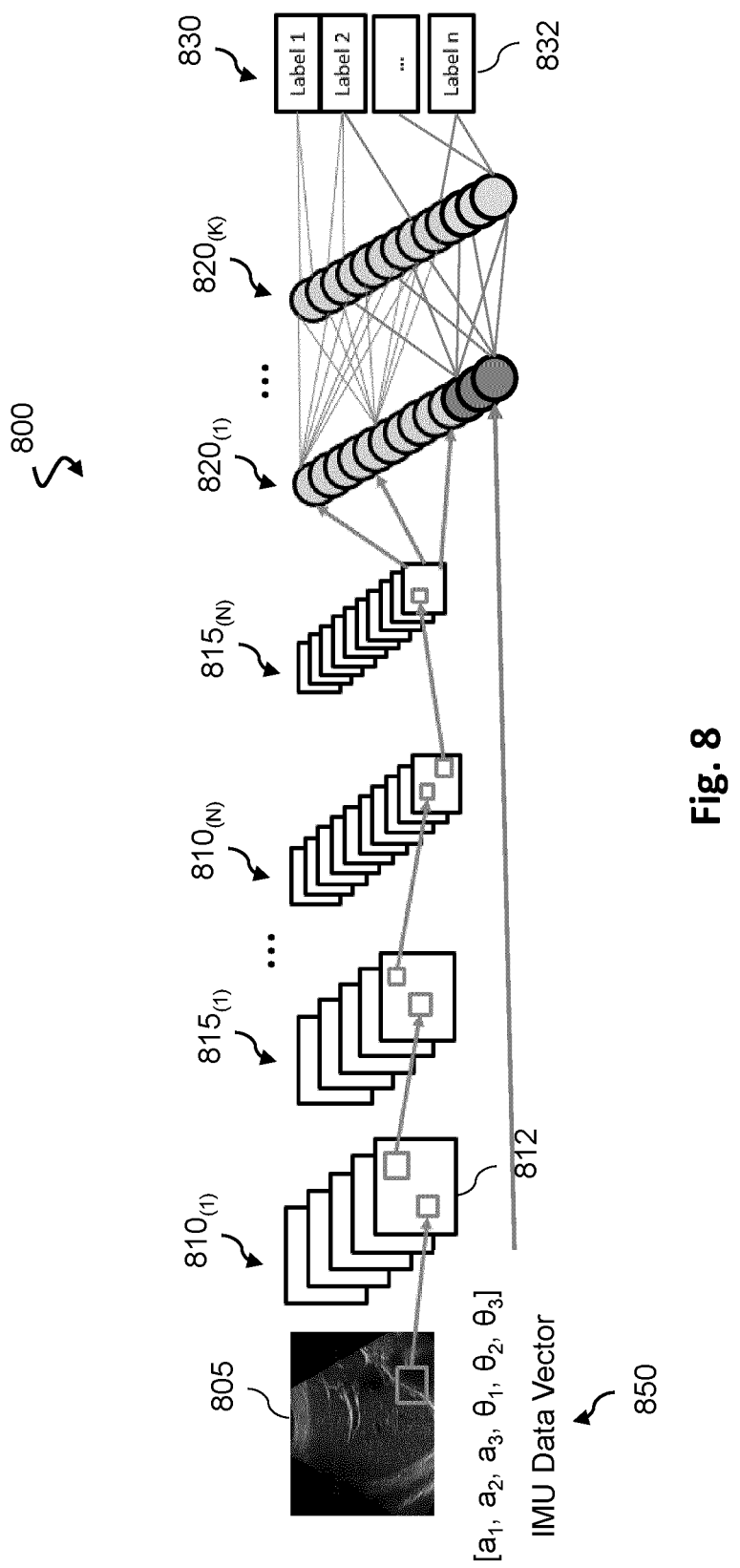
FIG. 8 is a schematic diagram of a deep learning network, according to aspects of the present disclosure.

Turning now to FIG. 8, a schematic diagram of a deep learning network is illustrated, according to aspects of the present disclosure. In particular, FIG. 8 illustrates a convolutional neural network (CNN) configuration 800 implemented as the deep learning network. For the purposes of example, the deep learning network may be described herein as a CNN, but embodiments are not limited thereto. For instance, the deep learning network may additionally or alternatively be implemented with a random forest deep learning approach, a regression analysis approach, or any other suitable approach or structure. Moreover, the present disclosure can include aspects described with respect to deep-learning based ultrasound imaging, including using IMU data, in U.S. Provisional application Ser. No. 63/127, 429, filed on an even date herewith, and titled "ULTRASOUND IMAGE-BASED IDENTIFICATION OF ANATOMICAL SCAN WINDOW, PROBE ORIENTATION, AND/OR PATIENT POSITION", the entirety of which is incorporated by reference herein.

In an embodiment, the configuration 800 may be trained to perform a classification task. More specifically, the configuration 800 may be trained to identify an acoustic window as corresponding to a zone of dome, a zone of apposition, or neither the zone of dome nor the zone of apposition. Moreover, the configuration 800 may be trained to perform the classification based on a combination of inputs, such as imaging data (e.g., ultrasound imaging data), IMU data, an input from the tracking system 142, a user input, and/or the like.

For instance, the configuration 800 may be trained to identify the acoustic window as corresponding to the zone of dome based on image features of the imaging data, IMU data and/or an input from the tracking system 142 corresponding to subcostal imaging, the user input, or a combination thereof. With respect to the imaging data, the configuration 800 may be trained to identify the acoustic window as corresponding to the zone of dome based on a portion of a diaphragm and/or a liver being included in the imaging data. The configuration 800 may additionally or alternatively be trained to identify the acoustic window as corresponding to the zone of dome based on determining the position and/or orientation of the probe 110 corresponds to subcostal imaging. For instance, the tracking system 142 may provide an indication of whether the ultrasound probe is positioned for subcostal imaging based on image or electromagnetic data collected at the tracking system, and the configuration 800 may identify the acoustic window as corresponding to the zone of dome based on an indication that the ultrasound probe is positioned for subcostal imaging. Additionally or alternatively, the tracking system 142 may provide the image and/or data associated with the magnetic field of the ultrasound probe to the configuration 800, which may identify the acoustic window based on the image and/or the data. For instance, the configuration 800 may be trained to associate the image and/or data with an acoustic window corresponding to the zone of dome, and/or the configuration 800 may be trained to determine the position and/or orientation of the probe 110 based on the image and/or the data and may then identify the acoustic window based on the determined position and/or orientation. Further, in some embodiments, the IMU 117 may provide an indication of whether the ultrasound probe is positioned for subcostal imaging, and, as similarly described above, the configuration 800 may identify the acoustic window as corresponding to the zone of dome based on an indication that the ultrasound probe is positioned for subcostal imaging. Moreover, the configuration 800 may identify the acoustic window as corresponding to the zone of dome based on the user input. For instance, the configuration 800 may associate a user input indicating a relatively greater depth setting (e.g., with respect to a depth setting used to image a zone of apposition), a user input indicating zone of dome and/or subcostal imaging, and/or the like with an acoustic window corresponding to the zone of dome.

The configuration 800 may be trained to identify the acoustic window as corresponding to the zone of apposition based on image features of the ultrasound imaging data, IMU data and/or an input from the tracking system 142 corresponding to intercostal imaging, the user input, or a combination thereof. With respect to the imaging data, the configuration 800 may be trained to identify the acoustic window as corresponding to the zone of apposition based on a portion of a diaphragm, lung tissue, and/or muscle tissue being included in the imaging data. The configuration 800 may additionally or alternatively be trained to identify the acoustic window as corresponding to the zone of apposition based on determining the position and/or orientation of the probe 110 corresponds to intercostal imaging. For instance, the tracking system 142 may provide an indication of whether the ultrasound probe is positioned for intercostal imaging based on image or electromagnetic data collected at the tracking system, and the configuration 800 may identify the acoustic window as corresponding to the zone of apposition based on an indication that the ultrasound probe is positioned for intercostal imaging. Additionally or alternatively, the tracking system 142 may provide the image and/or data associated with the magnetic field of the ultrasound probe to the configuration 800, which may identify the acoustic window based on the image and/or the data. For instance, the configuration 800 may be trained to associate the image and/or data with an acoustic window corresponding to the zone of apposition, and/or the configuration 800 may be trained to determine the position and/or orientation of the probe 110 based on the image and/or the data and may then identify the acoustic window based on the determined position and/or orientation. Further, in some embodiments, the IMU 117 may provide an indication of whether the ultrasound probe is positioned for intercostal imaging, and, as similarly described above, the configuration 800 may identify the acoustic window as corresponding to the zone of apposition based on an indication that the ultrasound probe is positioned for intercostal imaging. Moreover, the configuration 800 may identify the acoustic window as corresponding to the zone of apposition based on the user input. For instance, the configuration 800 may associate a user input indicating a relatively shallower depth setting (e.g., with respect to a depth setting used to image a zone of dome), a user input indicating zone of apposition and/or intercostal imaging, and/or the like with an acoustic window corresponding to the zone of apposition.

Similarly, the configuration 800 may be trained to identify the acoustic window as corresponding to neither the zone of dome nor the zone of apposition based on image features of the imaging data, IMU data and/or an input from the tracking system 142, the user input, or a combination thereof. For instance, based on the ultrasound imaging data lacking a portion of the diaphragm, lung tissue, liver, and/or muscle tissue, the configuration 800 may determine that the acoustic window does not correspond to the zone of dome or the zone of apposition. Further, based on the position and/or orientation of the ultrasound probe (e.g., as determined based on data from the tracking system 142 and/or the IMU 117) the configuration 800 may determine that the acoustic window does not correspond to the zone of dome or the zone of apposition. For instance, the configuration 800 may determine that the position and/or orientation of the ultrasound probe does not correspond to intercostal and/or subcostal imaging. Moreover, a user input selecting a target anatomical feature different from the zone of apposition and the zone of dome may provide an indication to the configuration 800 that the acoustic window does not correspond to the zone of dome or the zone of apposition.

The configuration 800 may be of any suitable type and may include any suitable type or number of layers including but not limited to convolutional layers, fully connected layers, flatten vectors, or any other techniques or implementations of artificial intelligence systems. The embodiments shown and/or described with reference to FIG. 8 can be scaled to include any suitable number of CNNs (e.g., about 2, 3 or more). The configuration 800 can be trained for identification of various anatomical features, probe orientations, acoustic windows, and/or the like associated with received ultrasound images as described in greater detail below.

The CNN may include a set of N convolutional layers 810 where N is any positive integer, each layer followed by a pooling layer 815. The CNN may also include a set of K fully connected layers 820, where K may be any positive integer. In one embodiment, the fully connected layers 820 include at least two fully connected layers 820. The convolutional layers 810 are shown as $810_{(1)}$ to $810_{(N)}$. The pooling layers 815 are shown as $815_{(1)}$ to $815_{(N)}$. The fully connected layers 820 are shown as $820_{(1)}$ to $820_{(K)}$. Each convolutional layer 810 may include a set of filters 812 configured to extract features from an input 805 (e.g., ultrasound images or other additional data). The convolutional layers 810 may include convolutional kernels of different sizes and strides. The values N and K and the size of the filters 812 may vary depending on the embodiments.

In some instances, the convolutional layers $810_{(1)}$ to $810_{(N)}$, the pooling layers $815_{(1)}$ to $815_{(N)}$, and the fully connected layers $820_{(1)}$ to $820_{(K-1)}$ may utilize a leaky rectified non-linear (ReLU) activation function and/or a suitable activation function to introduce nonlinearity for learning and/or batch normalization. The pooling layers 815 may include max pooling or average pooling techniques. The fully connected layers 820 may be non-linear and may gradually shrink the high-dimensional output to a dimension of the prediction result (e.g., the classification output 830). Thus, the fully connected layers 820 may also be referred to as a classifier. In some embodiments, the fully convolutional layers 810 may additionally be referred to as perception or perceptive layers.

As further illustrated, the configuration may receive an IMU data vector 850 as an additional input. The IMU data vector 850 may include orientation information $(\theta_1, \theta_2, \theta_3)$ and position information $(a_1, a_2, a_3)$ of the ultrasound probe as two sets of three continuous variables. The orientation information may correspond to an angle of the ultrasound probe with respect to an arbitrary x-axis, a y-axis, and a z-axis of the ultrasound probe, respectively, and the position information may correspond to the position of the ultrasound probe with respect to a patient coordinate system. For instance, the patient coordinate system may be defined by a right-left axis, an anterior-posterior axis, and a cranio-caudal axis, and the variables of the position information $(a_1, a_2, a_3)$ may correspond to position information along a respective one of these axes. The IMU data vector 850 may also contain additional information related to the position of the ultra-sound probe such as acceleration or rotation coordinates. Many ultrasound probes are equipped with IMU data to provide accelerometer and gyroscope data in real-time. This data may be used to determine the probe's angulation relative to gravity, and to determine relative changes in probe rotation around all three probe axes over time. This data can be provided in addition to the image data 805 as input to the configuration 800. The probe orientation may also be determined based on an optical camera image taken and/or electromagnetic measurements of a strength of a magnetic field of the ultrasound probe detected at the time of ultrasound image acquisition via the tracking system 142, for example. The configuration 800 may embed the additional data vector for example by concatenating it with the first fully connected layer 820(j). Moreover, in some embodiments, the fully connected layers 820 may perform a regression task based on the additional data vector. For example, the deep learning network may output one continuous three-value coordinate corresponding to orientation and a second continuous three-value coordinate correspond to translation, as well as any other coordinates relating to the position of the probe at the time of image acquisition based on the IMU orientation data and/or data from the tracking system 142. Further, this additional IMU data may thus be used both at training and application/inference phases of the configuration 800.

The fully connected layers 820 may downsample and map received information (e.g., the input 805 and/or the IMU data vector 850) to a finite number of classes 832. In an embodiment, the final fully connected layer $820_{(K)}$ may be a final classification layer such as softmax to transform the net activations in the final output layer to a series of values that can be interpreted as probabilities.

The classification output 830 may indicate a confidence score or probability for each of a plurality of classes 832, based on the input image 805. In that regard, the configuration 800 can be a multi-class classification network. In an exemplary embodiment, the plurality of classes 832 include an acoustic window corresponding to the zone of dome of a diaphragm, an acoustic window corresponding to the zone of apposition of a diaphragm, and an acoustic window corresponding to neither the zone of dome nor the zone of apposition. Label 1 may be one such combination (e.g., zone of dome), label 2 is another combination (e.g., zone of apposition), and so on. The output 830 may further indicate how likely the input image 805 belongs to a particular class 832. For example, a high confidence score for label 1 and lower confidence scores for the other labels indicates that the output label of the configuration 800 for the input image 805 is label 1 (zone of dome). The confidence score may be of any suitable type. In one embodiment, the confidence score may be a probability (e.g., a decimal value between 0 and 1). In this way, the output of the CNN may be a likelihood value for each of the possible options. The option with the highest likelihood will be assigned to the image. In some instances, the highest likelihood value is compared to a threshold and the output label is assigned to image if the value satisfies the threshold. For example, if the highest likelihood value exceeds a minimum threshold, then the output label is assigned to the image. If the highest likelihood value is below the minimum threshold, no option will be selected or assigned, or a dedicated "unknown" label will be assigned. Additionally or alternatively, if the highest likelihood value is below the minimum threshold, a prompt for a user input confirming, rejecting, or overriding the classification (e.g., the label) may be output for display (e.g., at the display 132).

The label may then be updated based on a user input received in response to the prompt, for example. If the image is stored/archived, the label can be stored together and/or in association with the image.

In some embodiments, the configuration 800 can also output a feature vector at the output of the last convolutional layer $810_{(N)}$ or pooling layer $815_{(N)}$. The feature vector may indicate objects detected from the input image 805 or other data. For instance, the feature vector may indicate any of the parameters identified from the image 805. As an illustrative example, the feature vector may indicate the diaphragm, the liver, lung tissue, muscle tissue, and/or the like identified within the image 805.

In an embodiment of the present disclosure, the deep learning network may include a multi-class classification network. In such an embodiment, the multi-class classification network may include an encoder path. For example, the image 805 may be of a high dimensional image. The image 805 may then be processed with the convolutional layers 810 such that the size is reduced. The resulting low dimensional representation of the image 805 may be used to generate the feature vector described previously. The low dimensional representation of the image 805 may additionally be used by the fully connected layers 820 to regress and output one or more classes 832. In some regards, the fully connected layers 820 may process the output of the encoder or convolutional layers 810. The fully connected layers 820 may additionally be referred to as task layers or regression layers, among other terms.

Training the deep learning network (e.g., the configuration 800) may be accomplished with various different techniques. In one embodiment, training the deep learning network may be accomplished by creating a large dataset of sample ultrasound images of different acoustic windows, probe orientations and/or positions, and/or user inputs. The sample images may additionally be obtained from a large number of patients. In an embodiment in which a deep learning network is trained to identify image parameters such as acoustic windows from images depicting many different regions of interest, the sample images may depict a wide variety of regions of interest. In embodiments in which multiple deep learning networks are trained, each may be tasked with identifying image parameters of ultrasound images depicting only one region of interest. In such an embodiment, a large number of sample images selected for the training of one deep learning network may all depict the same type of region of interest, though each would still depict various acoustic windows and be obtained from a large number of different patients.

As an example of one embodiment of training, each sample image selected for the training of a deep learning network may be assigned a variable $I_k$. Each image $I_k$ may be assigned a label $L_k$, where $L_k$ corresponds to the acoustic window and/or probe orientation used for image acquisition of the image $I_k$. The deep learning network may be trained batch-wise, using batches of tuples $(I_k, L_k)$, where $I_k$ is a possibly preprocessed ultrasound image, and $L_k$ is a corresponding label representing the acoustic window and/or probe orientation used during acquisition of image $I_k$. Methods of generating the label $L_k$ are described below.

For training the network, random batches of tuples $(I_k, L_k)$ may be generated. The images may be forward-propagated through the deep learning network, creating a tentative label assignment $L_k'$ for each image. A loss function may be defined to measure the size of the error between $L_k$ and $L_k'$ for all labels in the batch. The error may then be back-propagated through the network and an optimizer is used to adjust the network's parameters in order to improve subsequent predictions. The training process may continue for a fixed number of iterations or until some convergence criterion is met. For example, the training process may continue until the error no longer improves for a specified number of iterations.

In one embodiment, the loss function used during the training of the deep learning network may measure whether the estimated angle of the probe and/or anatomical scan window of the probe is correct or incorrect. For example, given a finite set of labels that the deep learning network may be trained to identify, the network may assign probabilities for each of the classes. For instance, the network may assign a probability of 80% (e.g., 0.8) for one class and 1% (e.g., 0.01) for another class. Further, a sum of the probabilities for each of the classes may equal 100% (e.g., 1). The loss function may then determine an error metric indicating how well the network predicts with high likelihood the correct label and low likelihood the incorrect labels. The loss function may include various other features or steps. For example, in an embodiment in which the probe orientation is defined as various three-value coordinates as opposed to a finite set of labels, the loss function may include an error metric relating to the difference in degrees or radians between the predicted angle of the probe in any of the defined axes and the actual angle of the probe.

One method for obtaining the labels $L_k$ is by having expert sonographers assign the label $L_k$ at the time of image acquisition (prospectively) or at the time of image review (retrospectively).

Other methods of automatically providing a label $L_k$ for an image $I_k$ can be implemented using a tracking system. The tracking system can be an optical tracking system in some embodiments. Optical camera tracking may involve a photographic device used in conjunction with the ultrasound imaging system. For example, an optical camera can obtain images of the patient and the probe during image acquisition. The optical images depict the probe location on the patient's body and body positioning of the patient. Based on the probe location and body positioning, the processor circuit can determine the labels $L_k$ for anatomical scan window and/or probe orientation. For example, using image processing techniques, a processor circuit may identify the head and feet of patient as well as the left and right regions of the patient to create a coordinate system of the patient. The processor may then use similar image processing techniques to identify the coordinate system of the probe. The processor circuit may then compare the two coordinate systems to identify the probe orientation. In some embodiments, the system 100 may also identify various features within the image received from the photographic device to determine a scan window. In such an embodiment, the system 100 may use image processing techniques to identify the location of ribs or bones within the patient anatomy and determine the location and direction of the probe 110 in relation to those ribs or other bones.

Returning now to FIG. 7, at step 708, the method 700 includes determining whether the identified acoustic window corresponds to the zone of dome or the zone of apposition. If, at step 708, the acoustic window does not correspond to the zone of dome or the zone of apposition, the ultrasound imaging system 100 may provide a prompt to a user (e.g., a sonographer) to reposition the probe 110. For instance, if the diaphragm is not included in the image data corresponding to the first ultrasound energy (e.g., transmitted at step 704), the ultrasound imaging system 100 may provide a graphical representation at the display 132 indicating that the target anatomical feature is not included in the acoustic window. As such, the steps 702, 704, and/or 706 of the method 700 may be repeated until the acoustic is identified as corresponding to the zone of apposition or the zone of dome at step 708.

If the acoustic window is identified as corresponding to the zone of apposition at step 708, the method 700 may proceed to step 710. At step 710, the method 700 involves implementing a high frequency setting. For instance, the ultrasound imaging system 100 may control the array of acoustic elements (e.g., the transducer array 112) to transmit second ultrasound energy at a high frequency (e.g., a second frequency), such as a frequency between 8-12 MHz, and to receive echoes associated with the second ultrasound energy. In this way, the ultrasound imaging system 100 may generate an ultrasound image and/or ultrasound imaging data of the zone of apposition of a diaphragm of a patient. Moreover, the image quality of the ultrasound image and/or imaging data may be greater (e.g., in terms of resolution and/or another image quality factor) than an ultrasound image generated based on ultrasound transmission at a relatively lower frequency. As discussed above with reference to step 406 of method 400 (FIG. 4), the ultrasound imaging system 100 may determine the frequency of the high frequency setting based on the acoustic window being identified as corresponding to the zone of apposition.

At step 712, the method 700 involves segmenting the diaphragm. In particular, the method 700 may involve performing segmentation of a region of interest, such as the diaphragm or a portion thereof, included in an ultrasound image generated based on the high frequency setting (e.g., an ultrasound image generated at step 712). In some embodiments, the ultrasound imaging system 100 may segment a first and a second wall of the diaphragm, such as a top and a bottom wall of the diaphragm. The ultrasound imaging system 100 may employ image processing algorithms and/or techniques, such as the Hough transform, to segment the diaphragm. Additionally or alternatively, the ultrasound imaging system 100 may use artificial intelligence-based diaphragm detection, such as detection of the diaphragm via the configuration 800 of FIG. 8, to segment the diaphragm.

At step 714, the method 700 includes performing adaptive beam steering. More specifically, the method 700 may involve steering the transmission and/or reception of ultrasound energy to increase the signal strength of the echoes reflected by the diaphragm. That is, for example, the ultrasound imaging system 100 may determine a steering angle that produces the highest echogenicity and/or an echogenicity satisfying a threshold at the diaphragm and may then steer ultrasound transmission at the probe 110 based on the determined angle. For instance, the position and structure orientation of a diaphragm and, more specifically, the zone of apposition, may vary over a heterogeneous patient population (e.g., between adults, children, obese subjects, subjects with respiratory disorders, and/or the like). The position and structure orientation of the diaphragm may further vary over a respiration cycle, as illustrated in FIG. 3. With respect to the structure orientation, a diaphragm may be imaged as including three layers, as illustrated in FIG. 6B. In particular, the diaphragm may include a nonechogenic central layer, as well as two hyperechogenic layers (e.g., the parietal pleura and peritoneum). To that end, the orientation of the hyperechogenic layers with respect to a patient's skin surface and a transducer face at the skin surface may impact the visibility of the diaphragm. As an illustrative example, imaging of the parietal pleura and peritoneum with an acoustic incidence angle of approximately 90° may result in the diaphragm appearing as a hyperechoic structure, as desired, while a more oblique acoustic incidence angle may reduce the visibility of the diaphragm.

Figure 9:
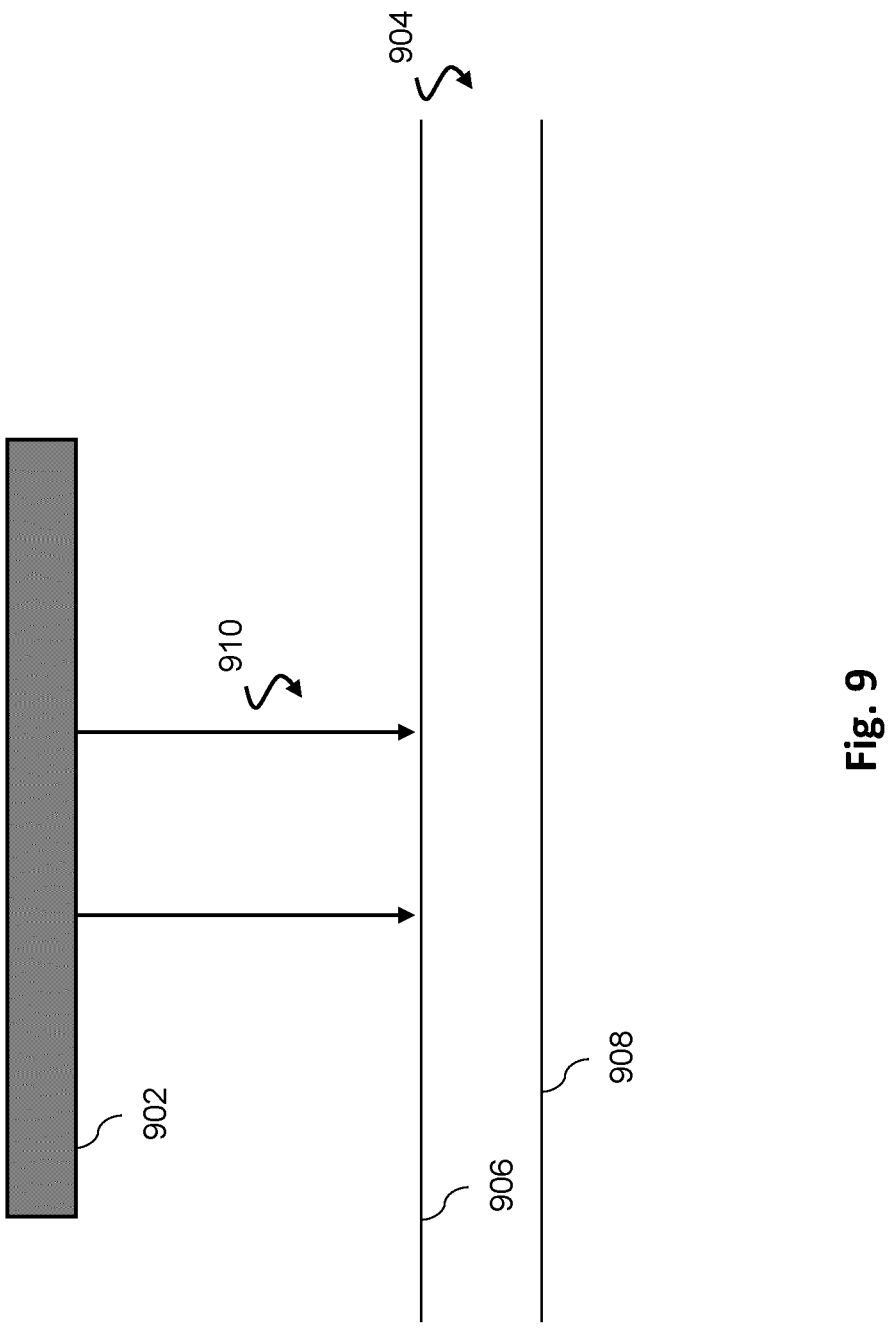
FIG. 9 is a schematic diagram of the transmission of ultrasound energy from a transducer array, according to aspects of the present disclosure.

FIG. 9 illustrates a schematic diagram of the transmission of ultrasound energy resulting in an acoustic incidence angle of approximately 90°. In particular, FIG. 9 illustrates a transducer array 902, which may be substantially similar to the transducer array 112, positioned relatively parallel with a diaphragm 904 and, in particular, the parietal pleura 906 (e.g., atop layer) and peritoneum 908 (e.g., a bottom layer) of the diaphragm 904. In some embodiments, the echoes associated with the ultrasound energy 910 may have a relatively high signal strength resulting from the acoustic incidence angle of approximately 90°. To that end, FIG. 6B may provide an illustrative example of an ultrasound image 650 resulting from the echoes associated with the ultrasound energy 910.

Figures 10A, 10B, 10C:
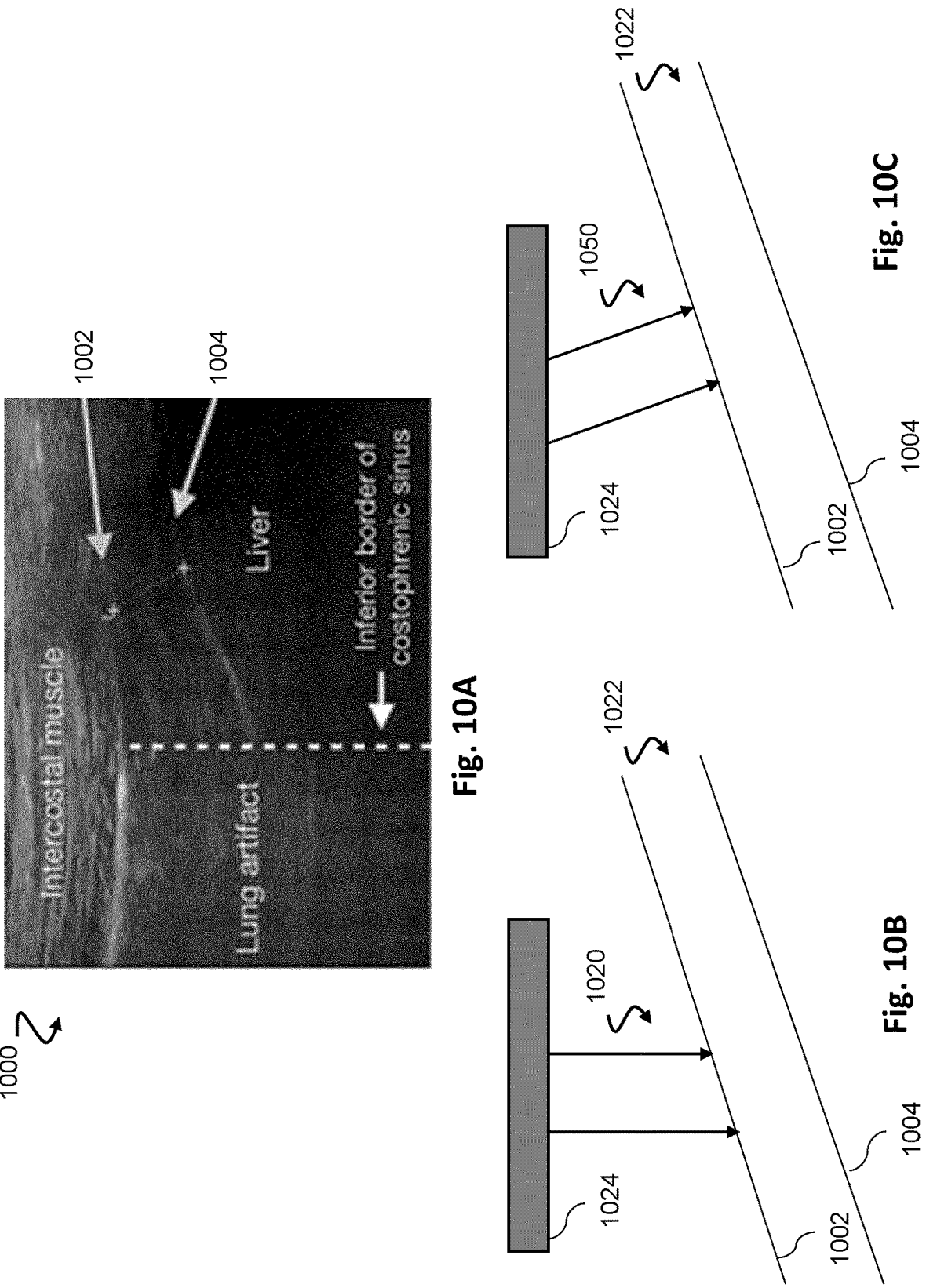
FIG. 10A is a diagrammatic view of an ultrasound image, according to aspects of the present disclosure.
FIG. 10B is a schematic diagram of the transmission of ultrasound energy from a transducer array, according to aspects of the present disclosure.
FIG. 10C is a schematic diagram of the transmission of ultrasound energy from a transducer array, according to aspects of the present disclosure.

For comparison, FIG. 10A illustrates an ultrasound image 1000 that may result from echoes associated with ultrasound energy transmission corresponding to an oblique acoustic incidence angle (e.g., an acoustic incidence angle exceeding or less than 90°). For instance, the ultrasound image 1000 may result from the transmission of the ultrasound energy 1020 to the diaphragm 1022 from the transducer array 1024 illustrated in FIG. 10B. As illustrated, the image quality of the ultrasound image 1000 of FIG. 10A is reduced in comparison with the ultrasound image 650 of FIG. 6B. The parietal pleura 656 and the peritoneum 658 within the ultrasound image 650 are more readily visible than the parietal pleura 1002 and the peritoneum 1004 of the ultrasound image 1000, for example. Further, the higher signal strength of the echoes received in association with the parietal pleura 656 and the peritoneum 658 of the ultrasound image 650 (FIG. 6B) may lead to more robust measurement of diaphragm thickness and/or other suitable metrics in comparison with measurements performed based on the signal strength of the echoes received in association with the parietal pleura 1002 and the peritoneum 1004 of the ultrasound image 1000, for example.

To that end, step 714 of the method 700 may involve determining a beam steering angle that provides an improved image quality, which may enable more robust measurements. For instance, in some embodiments, the step 714 may involve identifying a beam steering angle suitable to produce an acoustic incidence angle of approximately 90° for a given relationship between the position of the transducer array and the diaphragm 1022. More specifically, in some embodiments, step 714 of the method 700 may involve controlling the transducer array to consecutively fire (e.g., transmit ultrasound energy) at a series of beam steering angles. Step 714 may further involve determining, based on the echoes and/or image data associated with the series of beam steering angles, the beam steering angle that results in the highest echogenicity of the diaphragm and/or an echogenicity satisfying a threshold. That is, for example, the beam steering angle that results in the highest image quality and/or the best visibility of the diaphragm in the corresponding ultrasound image may be identified.

As an illustrative example, the transducer array 1024 may be controlled (e.g., via the ultrasound system 100) to transmit ultrasound energy at a series of different beam steering angles, which may include a first and second beam steering angle. For instance, the transmission of the ultrasound energy 1020 from the transducer array 1024 shown in FIG. 10B may represent the transmission of ultrasound energy at the first beam steering angle. The transmission of the ultrasound energy 1050 from the transducer array 1024 shown in FIG. 10C may represent the transmission of ultrasound energy at the different, second beam steering angle. Image data associated with the ultrasound energy 1020 transmitted at the first beam steering angle and image data associated with the ultrasound energy 1050 transmitted at the second beam steering angle may be analyzed via image processing, artificial intelligence (e.g., the configuration 800), and/or the like to identify the beam steering angle resulting in the highest echogenicity of the diaphragm and/or an echogenicity satisfying a threshold. For instance, the beam steering angle that produces the highest visibility (e.g., the highest contrast, sharpness, and/or resolution) of the parietal pleura and/or the peritoneum may be selected (e.g., set) as the beam steering angle for subsequent imaging by the transducer array 1024, such as imaging of the diaphragm 1022 to perform measurements of one or more characteristics of the diaphragm 1022. In some cases, the second beam steering angle illustrated in FIG. 10C may be selected, as the acoustic angle of incidence is approximately 90°.

Additionally or alternatively, a user input regarding the beam steering angle may be received (e.g., via the communication module 268), and the beam steering angle may be selected based on the user input. For instance, the user input may include a selection of the image data corresponding a particular beam steering angle, such as the image data corresponding to second beam steering angle.

Further, in some embodiments, the step 714 may involve adaptively beam steering based on movement of the diaphragm, such as movement of the diaphragm over a respiration cycle. For instance, the ultrasound imaging system 100 may determine a first beam steering angle suitable for imaging the diaphragm at the end of inspiration and a different, second beam steering angle suitable for imaging the diaphragm at the end of expiration. As such, the ultrasound imaging system 100 may control the transducer array 112 to transmit ultrasound energy in accordance with the first beam steering angle at the end of inspiration and may control the transducer array 112 to transmit ultrasound energy in accordance with the second beam steering angle at the end of expiration. In this way, the diaphragm may be well visualized in different stages of a respiration cycle. In some embodiments, for example, the ultrasound imaging system 100 may cycle through a set of beam steering angles previously determined by the ultrasound imaging system 100, such as the first and second beam steering angle, over a respiration cycle. In such cases, the ultrasound imaging system 100 may periodically determine whether to adjust a beam steering angle included in the set or may determine to adjust the beam steering angle in response to an event, such as the image quality of an image failing to satisfy a threshold. Additionally or alternatively, the ultrasound imaging system 100 may continuously determine and control the transducer array 112 to adapt the beam steering angle.

Moreover, in addition to or the alternative of adaptively beam steering (e.g., at step 714), the method 700 may involve tuning a different acoustic setting, such as a focal depth (e.g., a depth-dependent focus), a gain, and/or an imaging profile. For instance, the focal depth, gain and/or imaging profile may be adjusted based on the identification of the location of the diaphragm (e.g., based on the segmentation of the diaphragm at step 712).

Turning back to FIG. 7, at step 716, the method 700 may include determining a measurement associated with the zone of apposition. In particular, step 716 of the method may involve imaging the zone of apposition according to the beam steering angle or set of beam steering angles determined at step 714. Moreover, the measurement associated with the zone of apposition may include a measure of diaphragm thickness, which may correspond to the distance between the parietal pleura and the peritoneum. In particular, the measurement may include a thickness of the diaphragm at the end of inspiration and/or at the end of expiration, and/or the measurement may include a diaphragm thickening fraction (DTF). The DTF may be determined based on the difference between the thickness of the diaphragm at the end of inspiration and the thickness of the diaphragm at the end of expiration divided by the thickness of the diaphragm at the end of expiration (e.g., Diaphragm Thickness at the end inspiration–Diaphragm thickness at end expiration)/ (Diaphragm thickness at end expiration)).

Figure 11A:
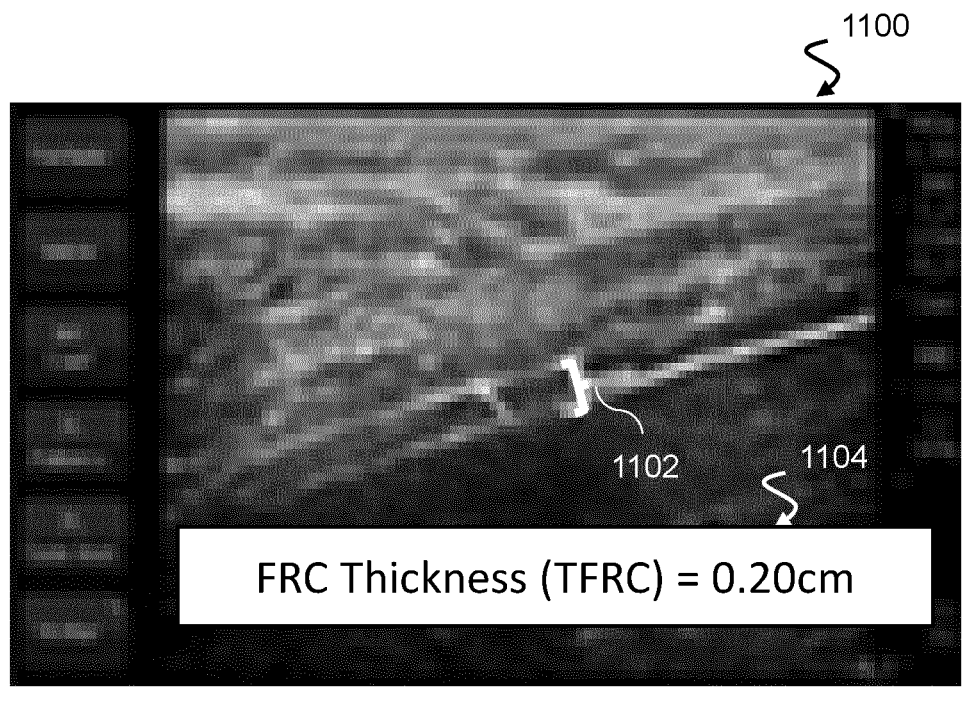
FIG. 11A is a diagrammatic view of an ultrasound image including a measurement of diaphragm thickness, according to aspects of the present disclosure.
Figure 11B:
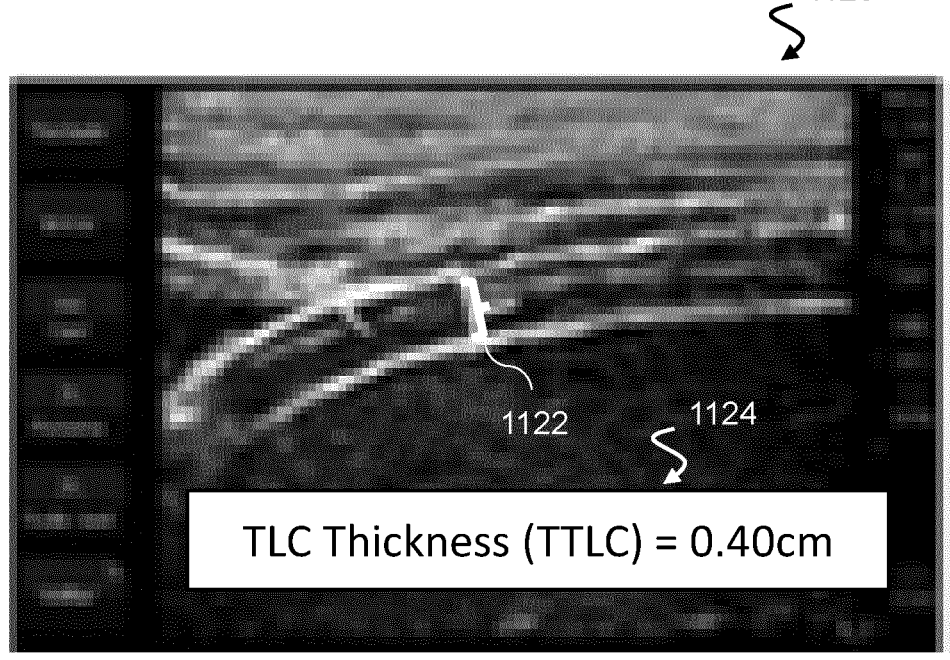
FIG. 11B is diagrammatic view of an ultrasound image including a measurement of diaphragm thickness, according to aspects of the present disclosure.

As an illustrative example, FIG. 11A shows an ultrasound image 1100 with the diaphragm thickness at the end of expiration (e.g., the functional residual capacity (FRC) thickness) denoted by a bracket 1102. Similarly, FIG. 11B— illustrates an ultrasound image 1120 with the diaphragm thickness at the end of inspiration (e.g., the total lung capacity (TLC) thickness) denoted by a bracket 1122.

In some embodiments, the ultrasound imaging system 100 may determine the measurement (e.g., at step 716) via image processing and/or via the configuration 800. For instance, the configuration 800 may be trained to identify the parietal pleura and the peritoneum and/or the parietal pleura and the peritoneum may be identified via segmentation, as described above. The distance between the parietal pleura and the peritoneum may then be determined. Moreover, a scale for the measurement may be provided at the ultrasound imaging system 100 (e.g., via a user input), may be determined based on a reference marker, such as a ruler or an anatomical feature having a known dimension, may be determined based on an acoustic setting (e.g., the depth setting) used to acquire the ultrasound image used in the measurement, and/or the like. The configuration 800 may further determine a confidence metric (e.g., confidence score) associated with the measurement. The confidence metric may be a decimal value between 0 and 1, for example, where a value of 1 indicates a higher probability that the measurement is accurate and a value of 0 indicates a lower probability that the measurement is accurate or vice versa.

Further, in some embodiments, the measurement may correspond to an elastography measurement (e.g., a measure of elasticity). For instance, the ultrasound imaging system 100 may determine a shear wave velocity associated with the diaphragm, which may correspond to a measure of stiffness of the diaphragm. Moreover, in some embodiments the measurement may correspond to a contraction velocity of the diaphragm. To that end, while the measurement associated with the zone of apposition is described herein as being a measure of thickness, DTF, an elastography measurement, or a contraction velocity, embodiments are not limited thereto. Instead, any suitable measurement may be determined.

At step 718, the method 700 includes outputting the measurement. More specifically, a graphical representation of the measurement may be output to a display. For instance, the ultrasound imaging system 100 may output a symbol, alphanumeric text, an icon and/or the like representing the thickness of the diaphragm at the end of inspiration and/or at the end of expiration and/or a diaphragm thickening fraction (DTF) to the display 132. As further shown in FIGS. 11A-B, the graphical representation may be overlaid upon an ultrasound image. In particular, FIG. 11A includes a first graphical representation of the measurement in the form of the bracket 1102, as well as a second graphical representation in the form of the message 1104. Similarly, FIG. 11B includes a first graphical representation of the measurement in the form of the bracket 1122, as well as a second graphical representation in the form of the message 1124. In this way, an indication of the health and/or function of the diaphragm may be provided at the display 132.

The measurement may additionally or alternatively be output in the form of a report. For instance, the ultrasound imaging system 100 may generate a thickness report, which may include information regarding the DTF, the diaphragm thickness at the end of inspiration, the diaphragm thickness at the end of expiration, and/or the like. The ultrasound imaging system 100 may further generate an elasticity report, which may include information regarding the shear wave velocity measured in association with the diaphragm.

If, at step 708 of the method 700, the acoustic window is identified as corresponding to the zone of dome, the method 700 may proceed to step 720. At step 720, the method 700 involves implementing a low frequency setting. For instance, the ultrasound imaging system 100 may control the array of acoustic elements (e.g., the transducer array 112) to transmit second ultrasound energy at a low frequency (e.g., a second frequency), such as a frequency between 2-4 MHz, and to receive echoes associated with the second ultrasound energy. In this way, the ultrasound imaging system 100 may generate an ultrasound image and/or ultrasound imaging data of the zone of dome of a diaphragm of a patient. Moreover, the image quality of the ultrasound image and/or imaging data may be greater (e.g., in terms of penetration and/or another image quality factor) than an ultrasound image generated based on ultrasound transmission at a relatively higher frequency. As discussed above with reference to step 406 of method 400 (FIG. 4), the ultrasound imaging system 100 may determine the frequency of the low frequency setting based on the acoustic window being identified as corresponding to the zone of dome.

At step 722, the method 700 involves segmenting the diaphragm. In particular, the method 700 may involve performing segmentation of a region of interest, such as the diaphragm or a portion thereof, included in an ultrasound image generated based on the low frequency setting (e.g., an ultrasound image generated at step 720), as generally described above with reference to step 712.

At step 724, the method 700 includes performing adaptive beam steering. More specifically, the method 700 may involve steering the transmission and/or reception of ultrasound energy to increase the signal strength of the echoes reflected by the diaphragm. That is, for example, the ultrasound imaging system 100 may determine a steering angle that produces the highest echogenicity at the diaphragm and/or an echogenicity exceeding a threshold and may then steer ultrasound transmission at the probe 110 based on the determined angle, as generally described above with reference to step 714.

Moreover, in addition to or the alternative of adaptively beam steering (e.g., at step 724), the method 700 may involve tuning a different acoustic setting, such as a focal depth (e.g., a depth-dependent focus), a gain, and/or an imaging profile. For instance, the focal depth, gain and/or imaging profile may be adjusted based on the identification of the location of the diaphragm (e.g., based on the segmentation of the diaphragm 722). In particular, for a linear transducer array, which may be identified based on the user input, as described above, the imaging profile may be set for trapezoid imaging.

At step 726, the method 700 includes determining a measurement associated with the zone of dome. In particular, step 726 of the method may involve imaging the zone of dome according to the beam steering angle or set of beam steering angles determined at step 724. Moreover, the measurement associated with the zone of dome may include a measure of diaphragm excursion (DE), which may correspond to the global displacement of the diaphragm from the end of inspiration to the end of expiration. As such, the measurement may be determined based on M-mode imaging or speckle tracking techniques. For instance, the ultrasound imaging system 100 may track the movement of a set of points of the diaphragm or the entire portion of the diaphragm in the field of view over a respiration cycle to determine the diaphragm excursion. In particular, the configuration 800 may be trained to track the movement of the diaphragm and to determine the resulting diaphragm excursion. The configuration 800 may further determine a confidence metric (e.g., confidence score) associated with the measurement. The confidence metric may be a decimal value between 0 and 1, for example, where a value of 1 indicates a higher probability that the measurement is accurate and a value of 0 indicates a lower probability that the measurement is accurate or vice versa. Further, the measurement may correspond to an elastography measurement or any other suitable measurement of the zone of dome.

Figure 12A:
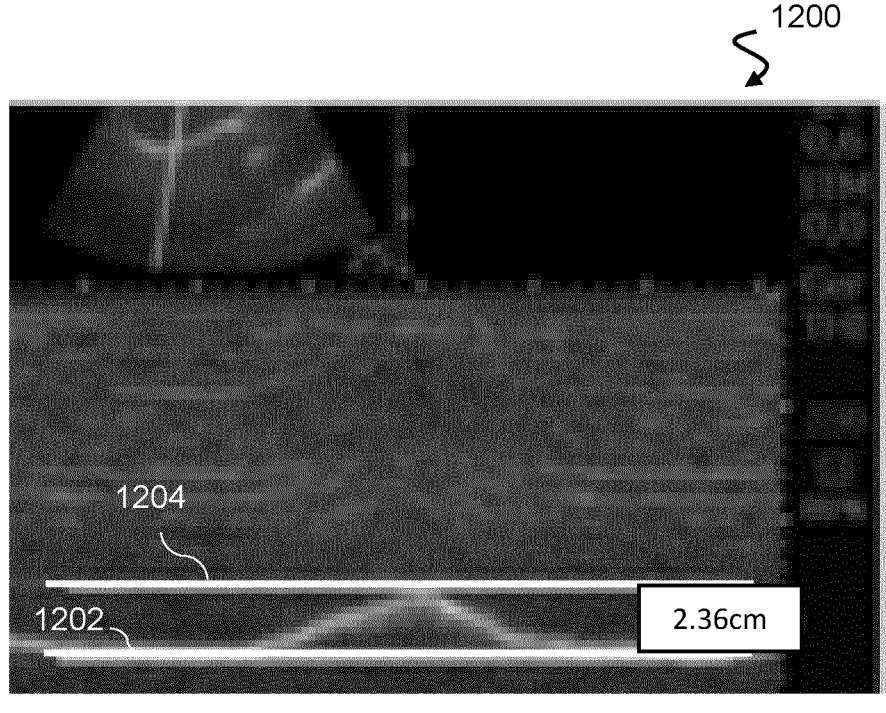
FIG. 12A is diagrammatic view of an ultrasound image including a measurement of diaphragm excursion, according to aspects of the present disclosure.
Figure 12B:
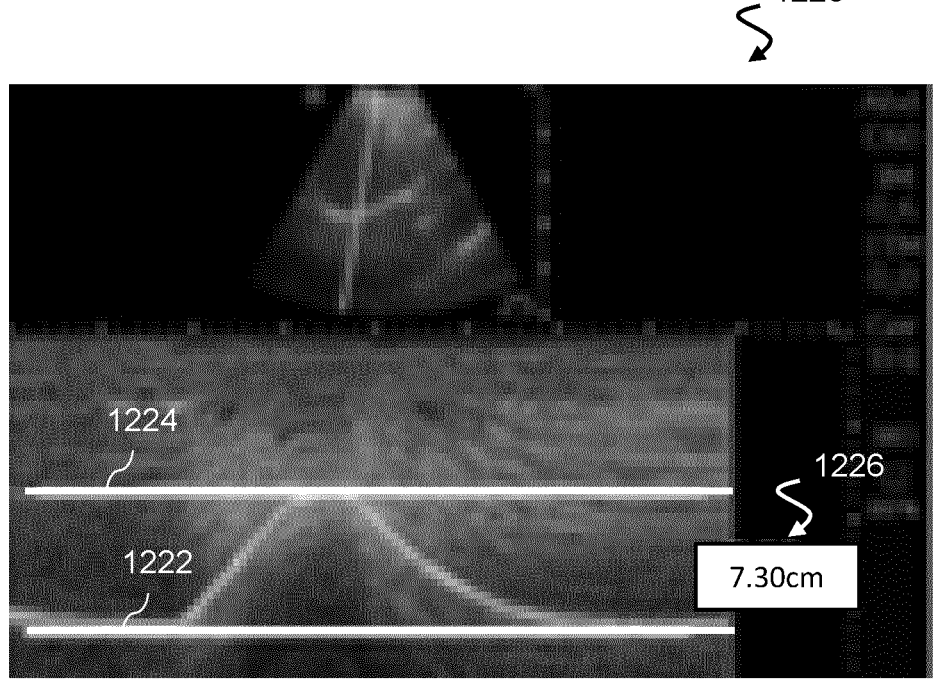
FIG. 12B is diagrammatic view of an ultrasound image including a measurement of diaphragm excursion, according to aspects of the present disclosure.

As an illustrative example, FIG. 12A shows an ultrasound image 1200 (e.g., an M-mode image) with the diaphragm excursion measured over a cycle of quiet breathing. As shown, the diaphragm or a portion thereof is displaced from a first position 1202 to a second position 1204 over the cycle of quiet breathing. FIG. 12B illustrates an ultrasound image 1220 (e.g., an M-mode image) with the diaphragm excursion measured over a cycle of deep breathing. As shown, the diaphragm or a portion thereof is displaced from a first position 1222 to a second position 1224 over the cycle of deep breathing.

At step 728, the method 700 involves outputting the measurement. More specifically, a graphical representation of the measurement may be output to a display. For instance, the ultrasound imaging system 100 may output a symbol, alphanumeric text, an icon and/or the like representing the diaphragm excursion to the display 132. As further shown in FIGS. 12A-B, the graphical representation may be overlaid upon an ultrasound image. In particular, FIG. 12A includes a first graphical representation of the measurement in the form of the indication of the first position 1202 and the second position 1204, as well as a second graphical representation in the form of the message 1206. Similarly, FIG. 12B includes a first graphical representation of the measurement in the form of the indication of the first position 1222 and second position 1224, as well as a second graphical representation in the form of the message 1226. In this way, an indication of the health and/or function of the diaphragm may be provided at the display 132.

The measurement may additionally or alternatively be output in the form of a report. For instance, the ultrasound imaging system 100 may generate an excursion report, which may include information regarding the diaphragm excursion over quiet breathing, deep breathing, slow breathing, fast breathing, and/or the like.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An ultrasound imaging system, comprising:
an array of acoustic elements; and
a processor circuit configured for communication with the array of acoustic elements, wherein the processor circuit is configured to:
control the array of acoustic elements to transmit first ultrasound energy at a first frequency and receive echoes associated with the first ultrasound energy;
automatically identify an acoustic window based on the echoes associated with the first ultrasound energy, wherein the acoustic window is associated with one of a subcostal location of the array and an intercostal location of the array;
determine a second frequency based on the automatically identified acoustic window;
control the array of acoustic elements to transmit second ultrasound energy at the second frequency and receive echoes associated with the second ultrasound energy;
generate an image based on the echoes associated with the second ultrasound energy; and
output the image to a display in communication with the processor circuit.

2. The ultrasound imaging system of claim 1, wherein the processor circuit is configured to identify the acoustic window further based on an orientation of the array of acoustic elements.

3. The ultrasound imaging system of claim 1, wherein the processor circuit is configured to identify the acoustic window further based on a user input.

4. The ultrasound imaging system of claim 3, wherein the user input comprises at least one of depth setting or a selection of an anatomical feature.

5. The ultrasound imaging system of claim 1, further comprising an inertial measurement unit (IMU) in communication with the processor circuit, wherein the processor circuit is configured to automatically identify the acoustic window further based on a position or orientation of the array collected at the IMU.

6. The ultrasound imaging system of claim 1, wherein the processor circuit is further configured to:
generate image data based on the echoes associated with the first ultrasound energy; and
detect an anatomical feature based on the image data, wherein the processor circuit is configured to identify the acoustic window further based on the anatomical feature.

7. The ultrasound imaging system of claim 1, wherein the processor circuit is further configured to:
determine a measurement of an anatomical feature included in the image; and
output a graphical representation of the measurement to the display.

8. The ultrasound imaging system of claim 7, wherein the measurement comprises at least one of a diaphragm excursion measurement, a diaphragm thickness measurement, or a diaphragm thickening fraction.

9. The ultrasound imaging system of claim 7, wherein the processor circuit is further configured to output a graphical representation of a confidence metric of the measurement to the display.

10. The ultrasound imaging system of claim 1, wherein the processor circuit is in communication with a tracking system configured to detect a position or orientation of the array, and wherein the processor circuit is configured to determine identify the acoustic window further based on the position or orientation of the array received from the tracking system.

11. The ultrasound imaging system of claim 1, wherein the processor circuit is further configured to select a beam steering angle from among a plurality of beam steering angles, wherein the processor circuit is configured to control the array of acoustic elements to transmit the second ultrasound energy further based on the beam steering angle.

12. The ultrasound imaging system of claim 11, wherein the processor circuit is configured to select the beam steering angle based on a comparison of an echogenicity of an anatomical feature at the beam steering angle and an echogenicity of the anatomical feature associated with an additional beam steering angle of the plurality of beam steering angles.

13. The ultrasound imaging system of claim 12, wherein the processor circuit is configured to select the beam steering angle further based on identifying a first wall and a second wall of the anatomical feature.

14. The ultrasound imaging system of claim 1, wherein the processor circuit is configured to determine an additional acoustic setting based on the acoustic window, wherein the processor circuit is configured to control the array of acoustic elements to transmit the second ultrasound energy further based on the additional acoustic setting.

15. A method of ultrasound imaging, comprising:

controlling, by a processor circuit, an array of acoustic elements in communication with the processor circuit to transmit first ultrasound energy at a first frequency and receive echoes associated with the first ultrasound energy;

automatically identifying, by the processor circuit, an acoustic window based on the echoes associated with the first ultrasound energy, and wherein the acoustic window is associated with one of a subcostal location of the array and an intercostal location of the array;

determining, by the processor circuit, a second frequency based on the automatically identified acoustic window;

controlling, by the processor circuit, the array of acoustic elements to transmit second ultrasound energy at the second frequency and receive echoes associated with the second ultrasound energy;

generating, by the processor circuit, an image based on the echoes associated with the second ultrasound energy; and outputting, by the processor circuit, the image to a display in communication with the processor circuit.

\* \* \* \* \*